(12) United States Patent
Seyedi et al.

(10) Patent No.: US 10,144,714 B2
(45) Date of Patent: Dec. 4, 2018

(54) METHODS OF MAKING PROTEIN DEACETYLASE INHIBITORS

(71) Applicant: Acetylon Pharmaceuticals, Inc., Boston, MA (US)

(72) Inventors: Farzaneh Seyedi, Mansfield, MA (US); John H. van Duzer, Georgetown, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 15/176,826

(22) Filed: Jun. 8, 2016

(65) Prior Publication Data

US 2016/0355486 A1     Dec. 8, 2016

Related U.S. Application Data

(60) Provisional application No. 62/172,624, filed on Jun. 8, 2015.

(51) Int. Cl.
  *C07D 239/42* (2006.01)
  *C07D 239/30* (2006.01)

(52) U.S. Cl.
  CPC ......... *C07D 239/42* (2013.01); *C07D 239/30* (2013.01)

(58) Field of Classification Search
  CPC .................................................. C07D 239/42
  USPC ....................................................... 544/332
  See application file for complete search history.

(56) References Cited

U.S. PATENT DOCUMENTS

| | | | |
|---|---|---|---|
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,994,362 B2 | 8/2011 | Schreiber et al. | |
| 8,148,526 B1 * | 4/2012 | van Duzer | C07C 259/06 544/332 |
| 8,394,810 B2 | 3/2013 | Van Duzer et al. | |
| 8,609,678 B2 | 12/2013 | Van Duzer et al. | |
| 8,614,223 B2 | 12/2013 | Van Duzer et al. | |
| 8,999,289 B2 | 4/2015 | Anderson et al. | |
| 9,096,549 B2 | 8/2015 | Van Duzer et al. | |
| 9,139,583 B2 | 9/2015 | Van Duzer et al. | |
| 9,145,412 B2 | 9/2015 | Van Duzer et al. | |
| 9,278,963 B2 | 3/2016 | Van Duzer et al. | |
| 9,421,212 B2 | 3/2016 | Van Duzer et al. | |
| 9,403,779 B2 | 8/2016 | Tamang et al. | |
| 9,409,890 B2 | 8/2016 | Van Duzer et al. | |
| 9,464,073 B2 | 10/2016 | Mazitschek et al. | |
| 9,562,013 B2 | 2/2017 | Van Duzer et al. | |
| 9,663,825 B2 | 5/2017 | Yang et al. | |
| 9,833,466 B2 | 12/2017 | Jones et al. | |
| 9,884,850 B2 | 2/2018 | Mazitschek et al. | |
| 2004/0266769 A1 | 12/2004 | Bressi et al. | |
| 2005/0119305 A1 | 6/2005 | Naka et al. | |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2009/0023786 A1 | 1/2009 | Miller et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |
| 2010/0330197 A1 | 12/2010 | Higashiguchi et al. | |
| 2011/0218154 A1 | 9/2011 | Schreiber et al. | |
| 2013/0225543 A1 | 8/2013 | Jones et al. | |
| 2014/0011767 A1 | 1/2014 | Yang et al. | |
| 2014/0142104 A1 | 5/2014 | Van Duzer et al. | |
| 2014/0142117 A1 | 5/2014 | Van Duzer et al. | |
| 2014/0357512 A1 | 12/2014 | Yang et al. | |
| 2015/0045380 A1 | 2/2015 | Van Duzer et al. | |
| 2015/0099744 A1 | 4/2015 | Yang et al. | |
| 2015/0105358 A1 | 4/2015 | Quayle et al. | |
| 2015/0105383 A1 | 4/2015 | Quayle et al. | |
| 2015/0105384 A1 | 4/2015 | Jones et al. | |
| 2015/0105409 A1 | 4/2015 | Quayle et al. | |
| 2015/0119413 A1 | 4/2015 | Gradilone et al. | |
| 2015/0150871 A1 | 6/2015 | Quayle et al. | |
| 2015/0176076 A1 | 6/2015 | Yang et al. | |
| 2015/0239869 A1 | 8/2015 | Mazitschek et al. | |
| 2015/0250786 A1 | 9/2015 | Berton et al. | |
| 2015/0299130 A1 | 10/2015 | Van Duzer et al. | |
| 2015/0359794 A1 | 12/2015 | Benz et al. | |
| 2016/0030458 A1 | 2/2016 | Jones et al. | |
| 2016/0137630 A1 | 5/2016 | Shearstone et al. | |
| 2016/0158231 A1 | 6/2016 | Jarpe et al. | |
| 2016/0158232 A1 | 6/2016 | Pozzi et al. | |
| 2016/0168093 A1 | 6/2016 | Van Duzer et al. | |

(Continued)

FOREIGN PATENT DOCUMENTS

| | | |
|---|---|---|
| WO | 2001/070675 A2 | 9/2001 |
| WO | 2002/074298 A1 | 9/2002 |

(Continued)

OTHER PUBLICATIONS

Butler et al. (2000) "Suberoylanilide hydroxamic acid, an inhibitor of histone deacetylase, suppresses the growth of prostate cancer cells in vitro and in vivo," Cancer Res. 60:5165-5170.

Costello et al. (Dec. 2012) "Evidence for Changes in RREB-1, ZIP3, and Zinc in the Early Development of Pancreatic Adenocarcinoma," J. Gastrointest. Canc. 43:570-578.

Del Amo et al. (2006) "General Preparation of Primary, Secondary, and Tertiary Aryl Amines by the Oxidative Coupling of Polyfunctional Aryl and Heteroaryl Amidocuprates," Angewandte Chemie, International Edition. 45(46):7838-7842.

Dokmanovic et al. (2007) "Histone Deacetylase Inhibitors: Overview and Perspectives," Mol. Cancer Res. 5(10):981-989.

(Continued)

*Primary Examiner* — Deepak R Rao
(74) *Attorney, Agent, or Firm* — Brian C. Trinque; Benjamin A. Vaughan; Lathrop Gage LLP

(57) ABSTRACT

The present invention relates to methods and intermediates useful for the synthesis of protein deacetylase inhibitors.

15 Claims, 11 Drawing Sheets

(56) References Cited

U.S. PATENT DOCUMENTS

| | | |
|---|---|---|
| 2016/0228434 A1 | 8/2016 | Reilly et al. |
| 2016/0279128 A1 | 9/2016 | Van Duzer et al. |
| 2016/0339022 A1 | 11/2016 | Tamang et al. |
| 2016/0346279 A1 | 12/2016 | Kavelaars et al. |
| 2016/0355486 A1 | 12/2016 | Seyedi et al. |
| 2017/0001965 A1 | 1/2017 | Van Duzer et al. |
| 2017/0020872 A1 | 1/2017 | Tamang et al. |
| 2017/0044144 A1 | 2/2017 | Van Duzer et al. |
| 2017/0096403 A1 | 4/2017 | Van Duzer et al. |
| 2017/0096413 A1 | 4/2017 | Mazitschek et al. |
| 2017/0327895 A1 | 11/2017 | Yang et al. |
| 2018/0036306 A1 | 2/2018 | Jones et al. |

FOREIGN PATENT DOCUMENTS

| | | |
|---|---|---|
| WO | 2003/037869 A1 | 5/2003 |
| WO | 2005/007091 A2 | 1/2005 |
| WO | 2006/102557 A2 | 9/2006 |
| WO | 2007/022638 A1 | 3/2007 |
| WO | 2007/130429 A2 | 11/2007 |
| WO | 2007/144341 A1 | 12/2007 |
| WO | 2008/003801 A1 | 1/2008 |
| WO | 2008/033746 A2 | 3/2008 |
| WO | 2008/091349 A1 | 7/2008 |
| WO | 2010/011296 A2 | 1/2010 |
| WO | 2010/131922 A2 | 11/2010 |
| WO | 2011/019393 A2 | 2/2011 |
| WO | 2011/084991 A2 | 7/2011 |
| WO | 2011/091213 A2 | 7/2011 |
| WO | 2011/146855 A1 | 11/2011 |
| WO | 2013/013113 A2 | 1/2013 |
| WO | 2013/048949 A2 | 4/2013 |
| WO | 2015/054099 A1 | 4/2015 |

OTHER PUBLICATIONS

Giannini et al. (Jul. 2012) "Histone Deacetylase Inhibitors in the Treatment of Cancer: Overview and Perspectives," Future Med. Chem. 4(11):1439-1460.

Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.

Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.

Lane et al. (2009) "Histone Deacetylase Inhibitors in Cancer Therapy," J. Clin. Oncol. 27:5459-5468.

Loudni et al. (2007) "Design, synthesis and biological evaluation of 1,4-benzodiazepine-2,5-dione-based HDAC inhibitors," Bioorganic and Medicinal Chemistry Letters. 17:4819-4823.

Mazitschek et al. (2008) "Development of a Fluorescence Polarization Based Assay for Histone Deacetylase Ligand Discovery," Bioorganic and Medicinal Chemistry Letters. 18(9):2809-2812.

Miller et al. (1998) "Paclitaxel as the Initial Treatment of Multiple Myeloma: An Eastern Cooperative Oncology Group Study (E1A93)," Am. J. Clin. Oncol. 21(6):553-556.

Miller et al. (2003) "Histone Deacetylase Inhibitors," J. Med. Chem. 46(24):5097-5116.

Monneret (2005) "Histone deacetylase inhibitors," Eur. J. Med. Chem. 40:1-13.

Perez (1998) "Paclitaxel in Breast Cancer," The Oncologist. 3:373-389.

Ramalingam et al. (2004) "Paclitaxel for non-small cell lung cancer," Exp. Opin. Pharmacother. 5(8):1771-1780.

Ropero et al. (2007) "The Role of Histone Deacetylases (HDACs) in Human Cancer," Molecular Oncology. 1:19-25.

Smil et al. (2009) "Novel HDAC6 Isoform Selective Chiral Small Molecule Histone Deacetylase Inhibitors," Bioorganic and Medicinal Chemistry Letters. 19:688-692.

Spanka et al. (2010) "Piperidyl amides as novel, potent and orally active mGlu5 receptor antagonists with anxiolytic-like activity," Bioorganic & Medicinal Chemistry Letters. 20(1):184-188.

Sporn et al. (2000) "Chemoprevention of Cancer," Carcinogenesis. 21(3):525-530.

Thoppil et al. (Sep. 2011) "Terpenoids as Potential Chemopreventive and Therapeutic Agents in Liver Cancer," World J. Hepatol. 3(9):228-249.

International Search Report with Written Opinion corresponding to International Patent Application No. PCT/US2011/021982, dated Oct. 12, 2011.

International Search Report with Written opinion corresponding to International Patent Application No. PCT/US2016/036434, dated Aug. 8, 2016.

Search Opinion corresponding to European Patent Application No. 11735212, dated Jun. 26, 2014.

Written Opinion corresponding to Singapore Patent Application No. Application No. 201205393-0, dated Nov. 15, 2013.

\* cited by examiner

| ¹H Signal Peak, ppm | Assigned Proton (Figure 1) |
|---|---|
| 10.35 (1H, s) | 19 |
| 8.76 (2H, s) | 10, 11 |
| 8.67 (1H, s) | 20 |
| 8.42 (1H, t, J=4.4Hz) | 12 |
| 7.62 (1H, dd, J1=7.6Hz, J2=2.0Hz) | 1 |
| 7.52 (1H, dd, J1 = 7.6 Hz, J2=2.0Hz) | 4 |
| 7.42 (6H, m, J=6.0Hz) | 2,3, 5, 6, 8, 9, |
| 7.21 (1H, tt, J1=7.2Hz, J2=1.6Hz) | 7 |
| 3.24 (2H, q) | 13 |
| 1.97 (2H, t, J=7.2Hz) | 18 |
| 1.49 (4H, m) | 14, 17 |
| 1.26 (4H, m) | 15, 16 |

METHODS OF MAKING PROTEIN DEACETYLASE INHIBITORS

RELATED APPLICATION

This application claims priority to U.S. Provisional Application No. 62/172,624, filed on Jun. 8, 2015, the content of which is incorporated herein by reference in its entirety.

BACKGROUND

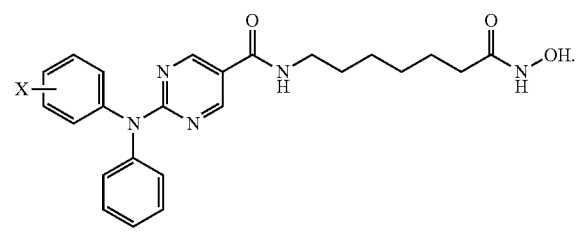

(I)

Compound (I) is disclosed in U.S. Pat. No. 8,148,526 as an HDAC inhibitor. Example 2 of U.S. Patent Application Publication No. 2015/0099744 discloses a synthesis of compound (I). As detailed herein in Example 3, this synthesis procedure resulted in the formation of significant amounts of de-chlorination and chlorine-migration side products. These impurities have solubilities that are similar to the solubilities of the desired intermediates. Removal of the impurities is very challenging, requiring lengthy work-ups, involving numerous washes, triturations and crystallizations. Triturations, in particular, are known to be inefficient and unscalable processes. When compound (I) was prepared according to Example 2, the necessary purification steps resulted in a significant loss of desired intermediates, led to a modest overall yield, and rendered further industrial scale up of the synthesis route unpractical. There remains a need for new methods for the synthesis of compound (I), and related compounds, that minimize the formation of impurities, and that are amenable to industrial scale-up.

SUMMARY

Accordingly, provided herein is an improved method of making compound (Ia).

(Ia)

The improved method entirely avoids the formation of de-chlorination and chlorine-migration impurities. Moreover, the improved method results in a higher (e.g., over double) yield of compound (I) (e.g., 15.7% overall yield by the method of Example 2, versus 40% overall yield by the improved method). Also provided are compounds useful as intermediates in the synthesis of compound (Ia) and compositions comprising said compounds.

In one aspect, provided herein is a method of making compound (Ia), the method comprising the steps of:

converting compound 11a into compound 3a:

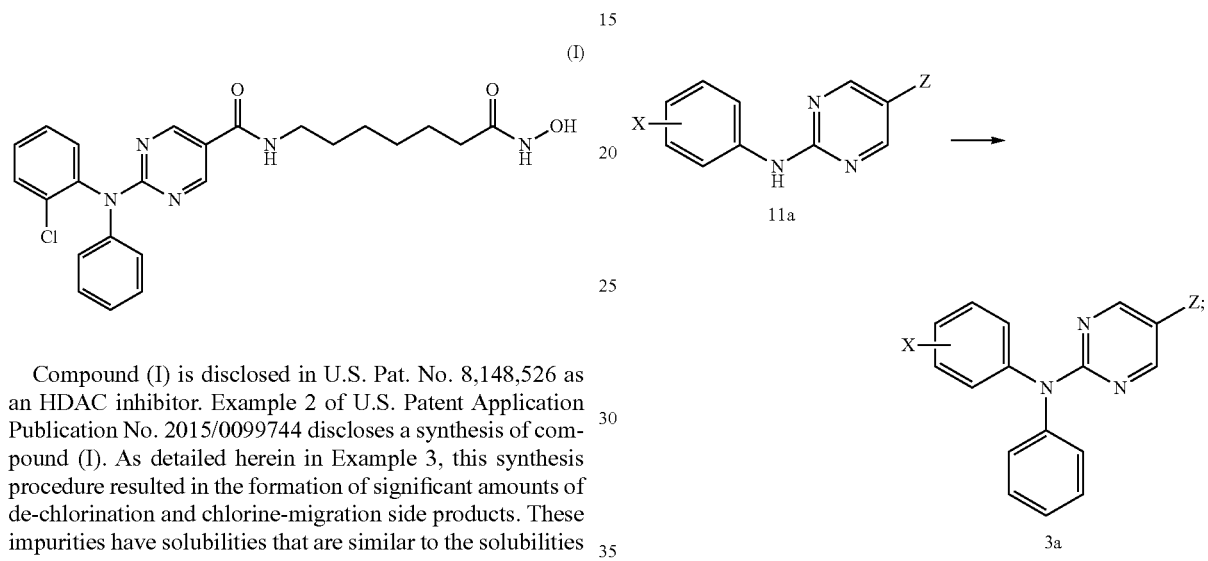

wherein X is selected from fluorine, chlorine, bromine and iodine;

Z is selected from the group consisting of —CN and —CO$_2$R; and

R is C$_1$-C$_6$ alkyl; and converting compound 3a into compound (Ia).

In one embodiment, compound 11a is prepared by a method comprising the step of:

converting compound 1a into compound 11a:

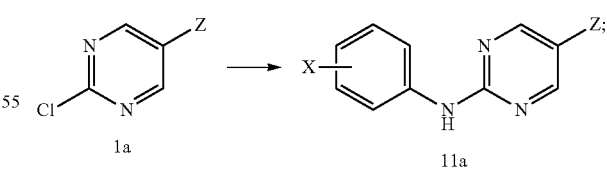

wherein X is selected from fluorine, chlorine, bromine and iodine;

Z is selected from the group consisting of —CN and —CO$_2$R; and

R is C$_1$-C$_6$ alkyl.

In another embodiment, the step of converting compound 3a into compound (Ia) comprises the steps of:

converting compound 3a into compound 4a:
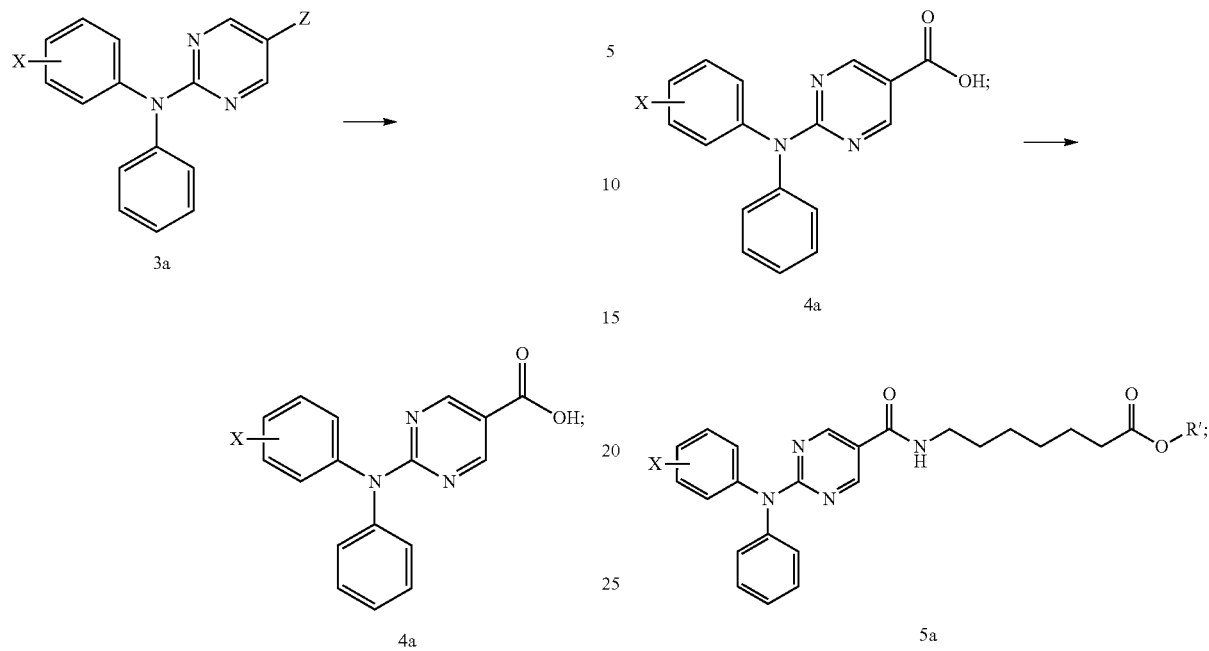
and
  converting compound 4a into compound (Ia).
In another embodiment, the step of converting compound 4a into compound (Ia) comprises the steps of:
converting compound 4a into compound 5a:
wherein X is selected from fluorine, chlorine, bromine and iodine; and
R' is $C_1$-$C_6$ alkyl; and
converting compound 5a into compound (Ia):
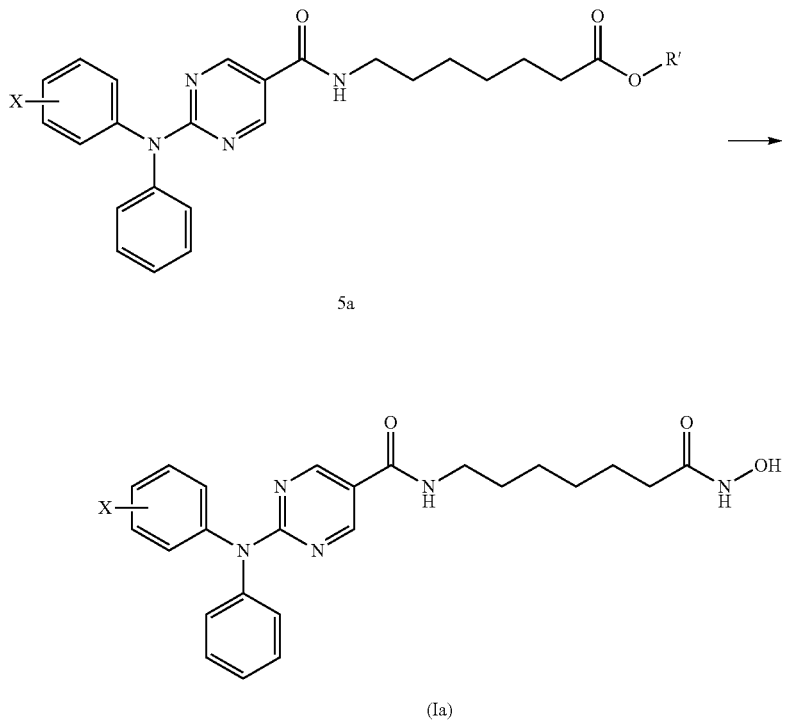

wherein X is selected from fluorine, chlorine, bromine and iodine.

In a particular embodiment of the method of making compound (Ia), X is chlorine. In another particular embodiment, Z is CO$_2$Et (i.e., R is ethyl). In another particular embodiment, R' is methyl.

In another aspect, provided herein is a method of making compound (I):

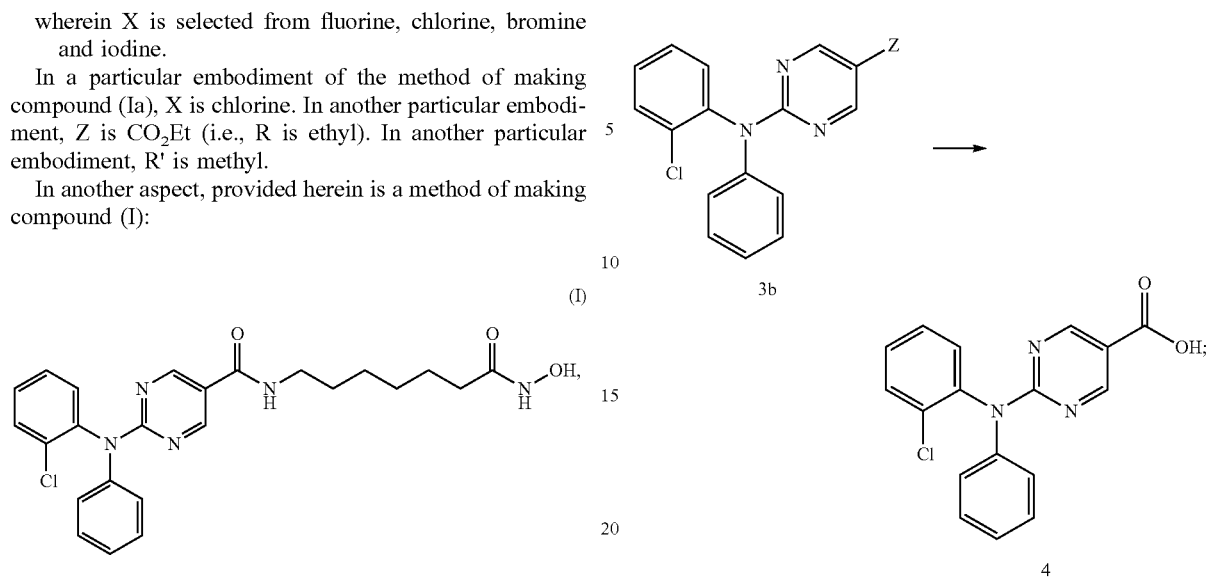

the method comprising the steps of:
converting compound 11b into compound 3b:

wherein Z is selected from the group consisting of —CN and —CO$_2$R; and wherein R is C$_1$-C$_6$ alkyl; and
converting compound 3b into compound (I).

In one embodiment, compound 11b is prepared by a method comprising the step of: converting compound 1b into compound 11b:

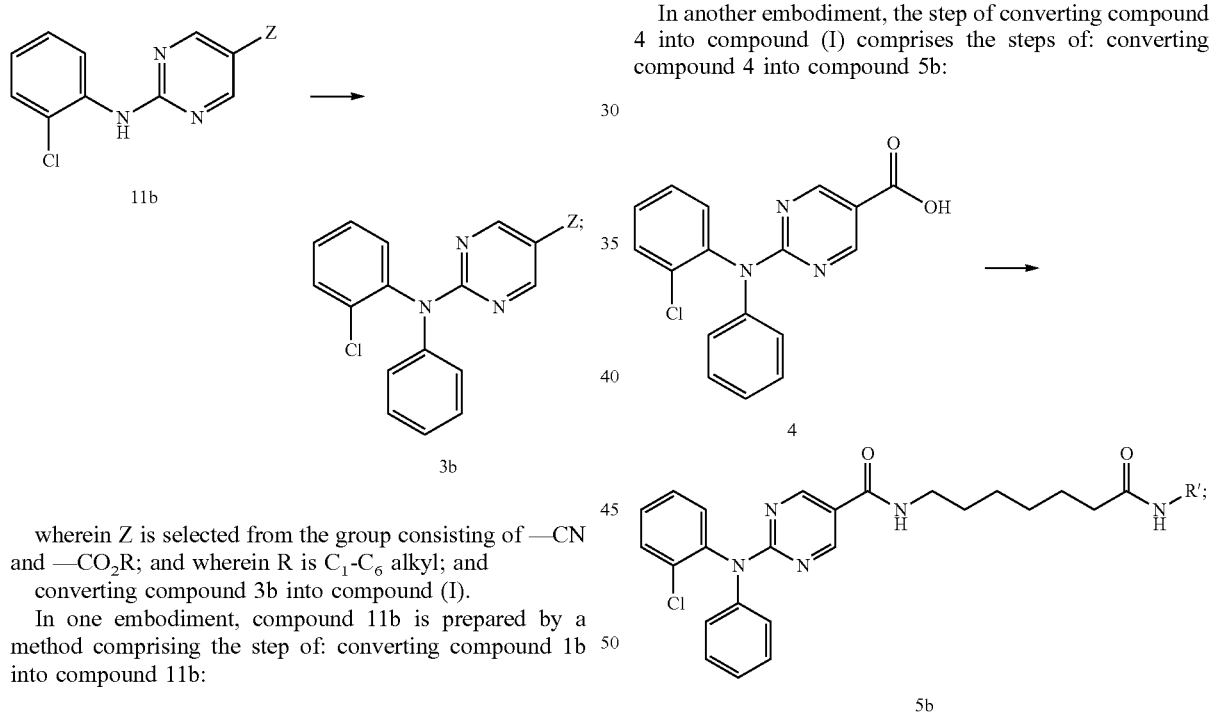

wherein Z is selected from the group consisting of —CN and —CO$_2$R; and wherein R is C$_1$-C$_6$ alkyl.

In another embodiment, the step of converting compound 3b into compound (I) comprises the steps of: converting compound 3b into compound 4:

and
converting compound 4 into compound (I).

In another embodiment, the step of converting compound 4 into compound (I) comprises the steps of: converting compound 4 into compound 5b:

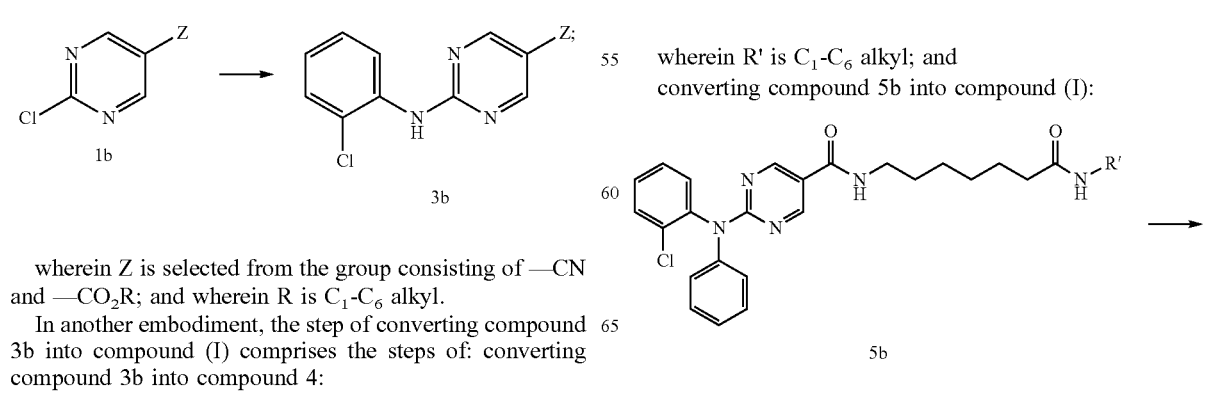

wherein R' is C$_1$-C$_6$ alkyl; and
converting compound 5b into compound (I):

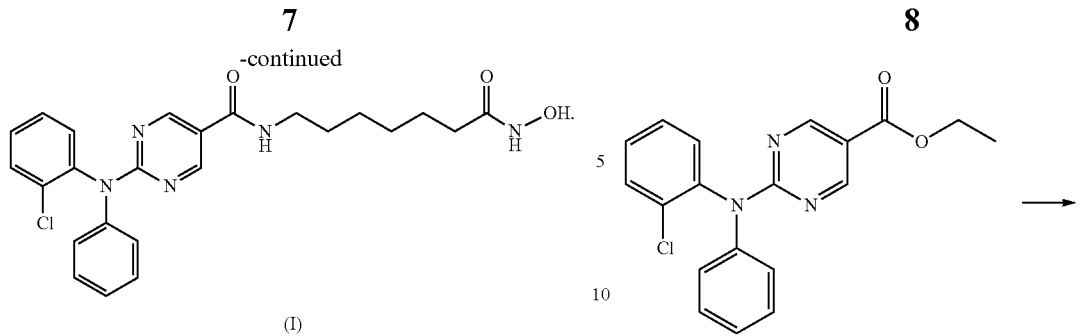

(I)

In a particular embodiment of the above methods, Z is CO₂Et (i.e., R is ethyl). In another particular embodiment, R' is methyl.

In a particular embodiment, the step of converting compound 1b into compound 11b comprises reacting compound 1 with 2-chloroaniline to obtain compound 11:

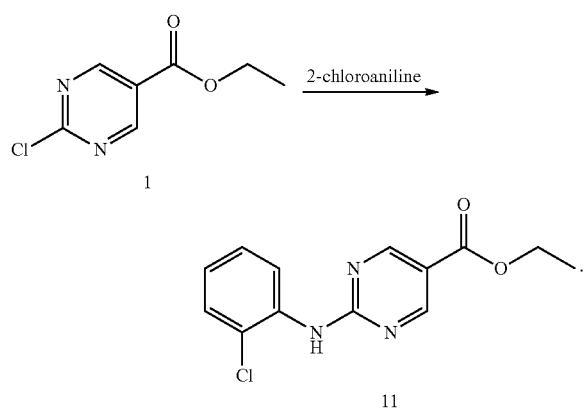

In another particular embodiment, the step of converting compound 11b into compound 3b comprises reacting compound 11 with iodobenzene to obtain compound 3:

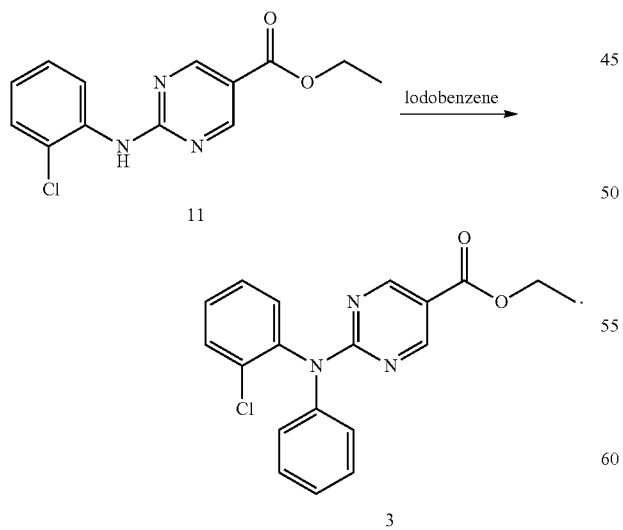

In another particular embodiment, the step of converting compound 3b into compound 4 comprises hydrolyzing the ester of compound 3:

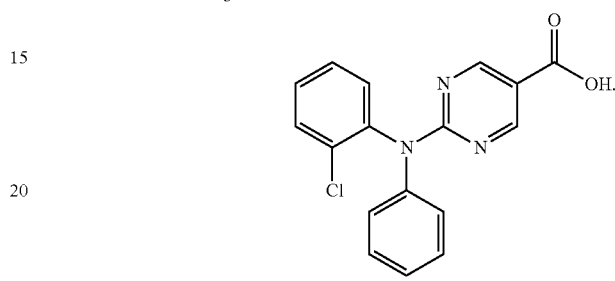

In another particular embodiment, the step of converting compound 4 into compound 5b comprises reacting compound 4 with methyl 7-aminoheptanoate to obtain compound 5:

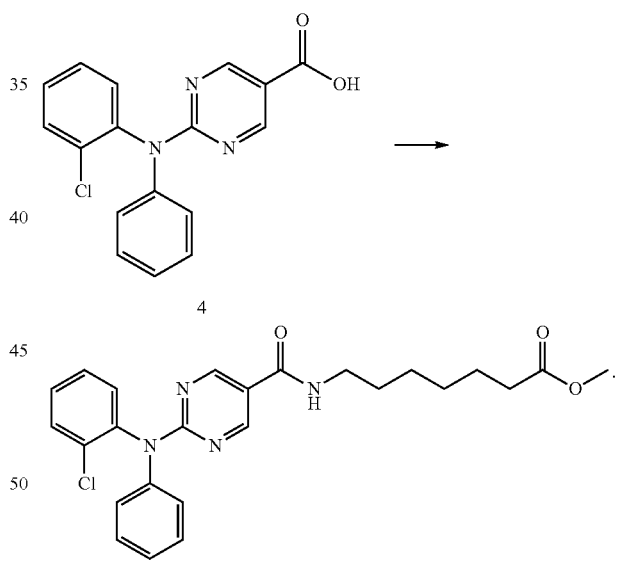

In another particular embodiment, the step of converting compound 5b into compound (I) comprises reacting compound 5 with hydroxylamine, or a salt thereof, to obtain compound (I), or a salt thereof.

In another aspect, provided herein is a method of making compound (I) comprising the steps:

(1) reacting ethyl 2-chloropyrimidine-5-carboxylate with 2-chloroaniline to obtain compound 11;
(2) reacting compound 11 with iodobenzene to obtain compound 3;
(3) reacting compound 3 with aqueous base, then with acid, to obtain compound 4;

(4) reacting compound 4 with methyl 7-aminoheptanoate to obtain compound 5; and (5) reacting compound 5 with hydroxylamine, or a salt thereof, to obtain compound (I), or a salt thereof.

In another aspect, provided herein is a compound having the structure of 11b:

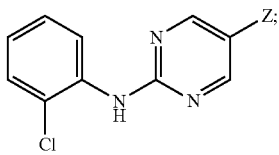

11b wherein Z is selected from the group consisting of —CN and —CO$_2$R; and wherein R is C$_1$-C$_6$ alkyl. In one embodiment, Z is —CO$_2$R. In a particular embodiment, Z is —CO$_2$R and R is ethyl. In another particular embodiment, compound 11b is compound 11.

In another aspect, provided herein is a composition comprising 1b and 11b, wherein 1b and 11b are defined above. In one embodiment of the composition, 1b is compound 1 and 11b is compound 11.

In another aspect, provided herein is a composition comprising 11b and 3b, wherein 11b and 3b are defined above. In one embodiment of the composition, 11b is compound 11 and 3b is compound 3.

In another aspect, provided herein is a composition comprising the compound 11b. In one embodiment, the composition further comprises compound 3.

In another aspect, provided herein is a composition comprising compound 3, wherein the composition is free from compounds de-Cl-3 and m-Cl-3:

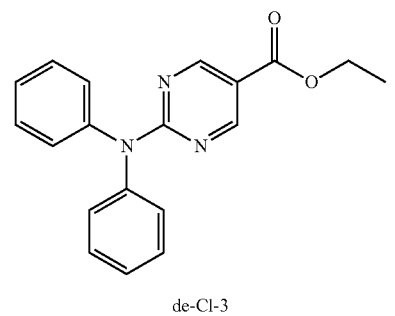

de-Cl-3

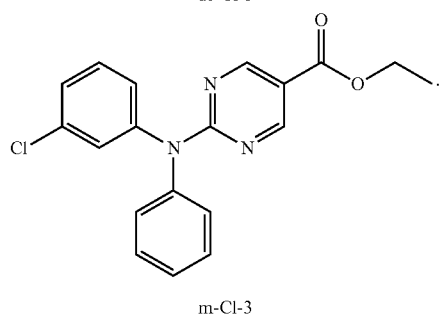

m-Cl-3

In another aspect, provided herein is a composition comprising compound 4, wherein the composition is free from compounds de-Cl-4 and m-Cl-4:

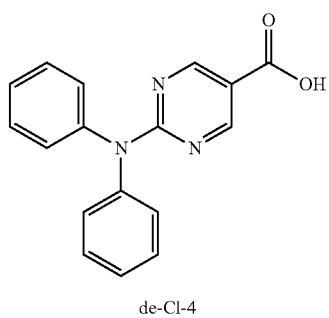

de-Cl-4

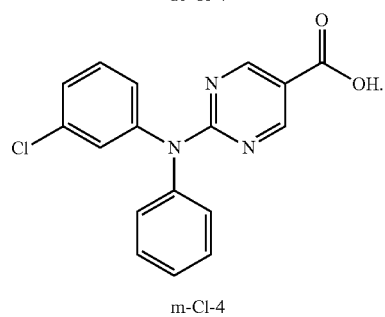

m-Cl-4

In another aspect, provided herein is a composition comprising compound 5, wherein the composition is free from compounds de-Cl-5 and m-Cl-5:

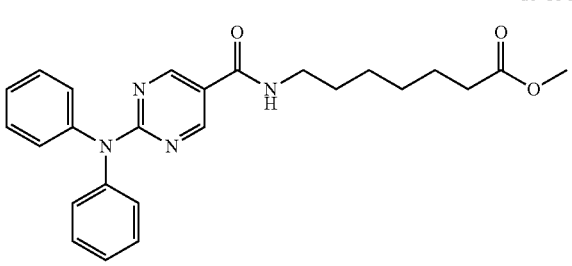

de-Cl-5

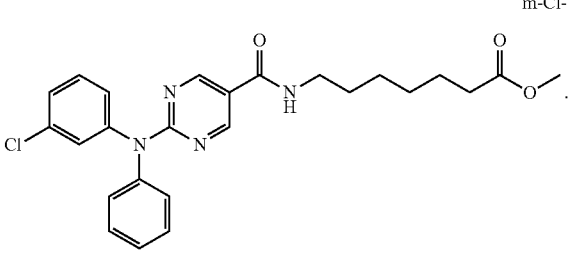

m-Cl-5

DETAILED DESCRIPTION OF THE INVENTION

Methods of Synthesis

Figure 1:
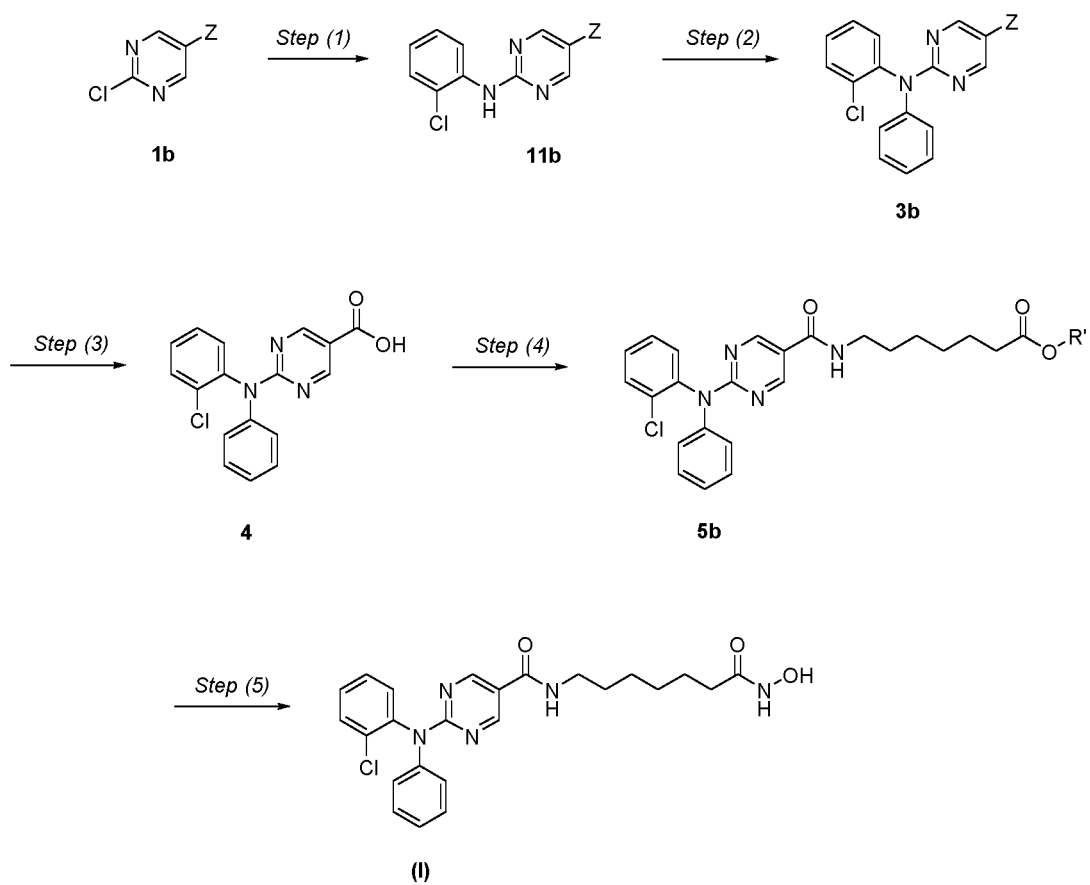
FIG. 1 depicts a generic synthesis of compound (I) according to the improved method described herein.

Provided herein, inter alia, is a method of making compound (Ia) comprising the steps of:

converting compound 11a into compound 3a:

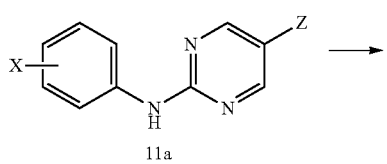

11a

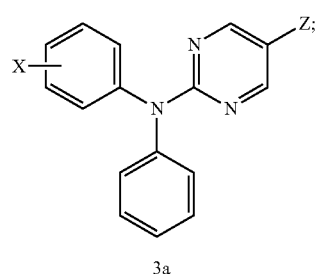

3a wherein X is selected from fluorine, chlorine, bromine and iodine;

Z is selected from the group consisting of —CN and —CO$_2$R; and

R is C$_1$-C$_6$ alkyl; and converting compound 3a into compound (Ia).

In one embodiment, compound 11a is prepared by a method comprising the step of:

converting compound 1a into compound 11a:

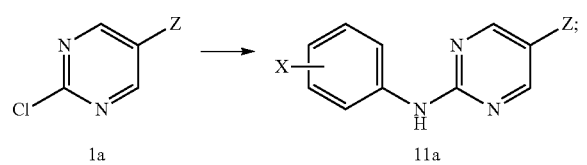

wherein X is selected from fluorine, chlorine, bromine and iodine;

Z is selected from the group consisting of —CN and —CO$_2$R; and

R is C$_1$-C$_6$ alkyl.

In another embodiment, the step of converting compound 3a into compound (Ia) comprises the steps of:

converting compound 3a into compound 4a:

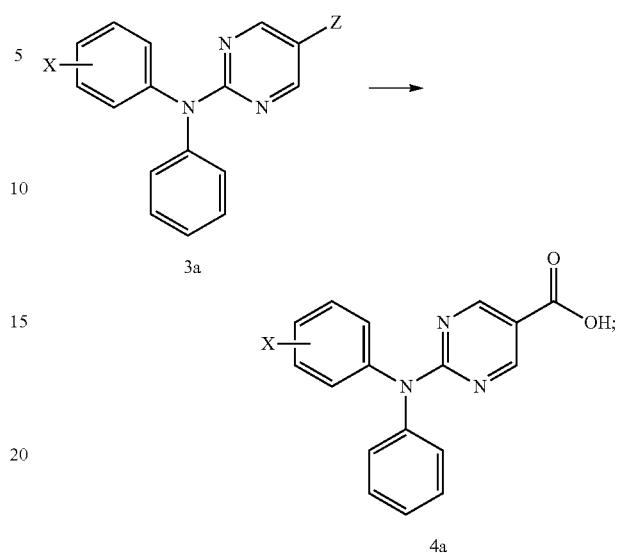

and converting compound 4a into compound (Ia).

In another embodiment, the step of converting compound 4a into compound (Ia) comprises the steps of:

converting compound 4a into compound 5a:

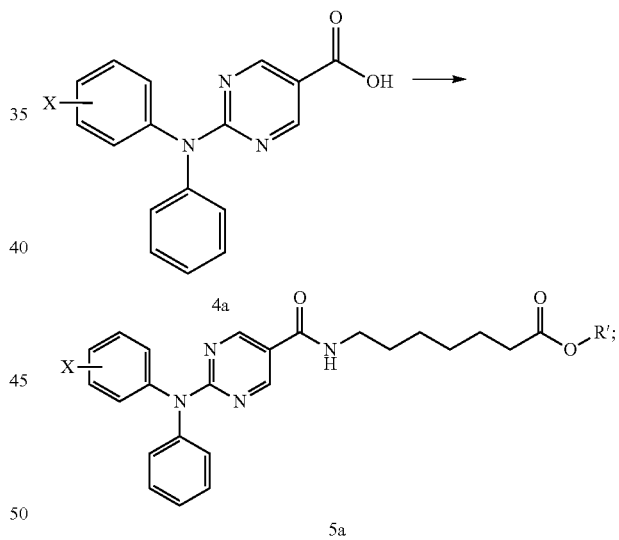

wherein X is selected from fluorine, chlorine, bromine and iodine; and

R' is C$_1$-C$_6$ alkyl; and converting compound 5a into compound (Ia):

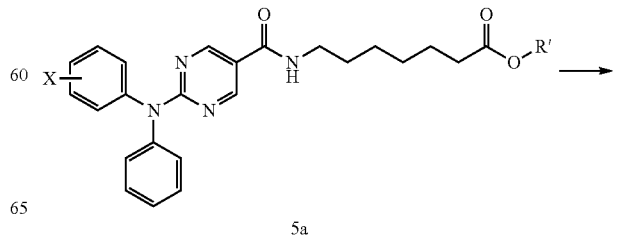

5a

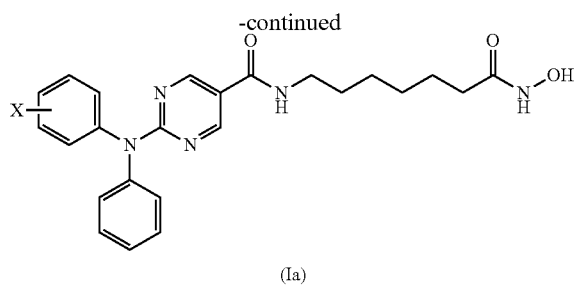

(Ia)

wherein X is selected from fluorine, chlorine, bromine and iodine.

In a particular embodiment of the method of making compound (Ia), X is chlorine. In another particular embodiment, Z is CO$_2$Et (i.e., R is ethyl). In another particular embodiment, R' is methyl.

With reference to FIG. 1, provided herein is a method of making compound (I), wherein Z is selected from the group consisting of —CN and —CO$_2$R, R is C$_1$-C$_6$ alkyl, and R' is C$_1$-C$_6$ alkyl. In certain embodiments of the method, R is C$_1$-C$_6$ alkyl. In a particular embodiment, R is ethyl. In another particular embodiment, R' is methyl.

In one embodiment, the method comprises the step of converting compound 1b to compound 11b, i.e., Step (1). In a particular embodiment, Step (1) comprises reacting compound 1b with 2-chloroaniline to obtain compound 11b.

In another embodiment, the method comprises the step of converting compound 11b to compound 3b, i.e., Step (2). In a particular embodiment, Step (2) comprises reacting compound 11b with iodobenzene to obtain compound 3b.

In another embodiment, the method comprises Steps (1)-(2), and the step of converting compound 3b to compound 4, i.e., Step (3). In a particular embodiment, Step (3) comprises forming a mixture of the product of Step (2) (i.e., the reaction mixture comprising compound 3b) and water, and heating the mixture.

In another embodiment, the method comprises Steps (1)-(3), and the step of converting compound 4 to compound 5b, i.e., Step (4). In a particular embodiment, Step (4) comprises reacting compound 4 with an ester of 7-aminoheptanoic acid to obtain compound 5b.

In another embodiment, the method comprises Steps (1)-(4), and the step of converting compound 5b to compound (I), i.e., Step (5). In a particular embodiment, Step (5) comprises reacting compound 5b with hydroxylamine, or a salt thereof, to obtain compound (I), or a salt thereof.

In another embodiment, the method comprises Steps (1)-(5).

In another embodiment, the method comprises Steps (1)-(2), with subsequent steps known in the art, such that compound (I), or a salt thereof, is formed. In another embodiment, the method comprises Steps (1)-(3) with subsequent steps known in the art, such that compound (I), or a salt thereof, is formed. In another embodiment, the method comprises Steps (1)-(4) with subsequent steps known in the art, such that compound (I), or a salt thereof, is formed.

Figure 2:
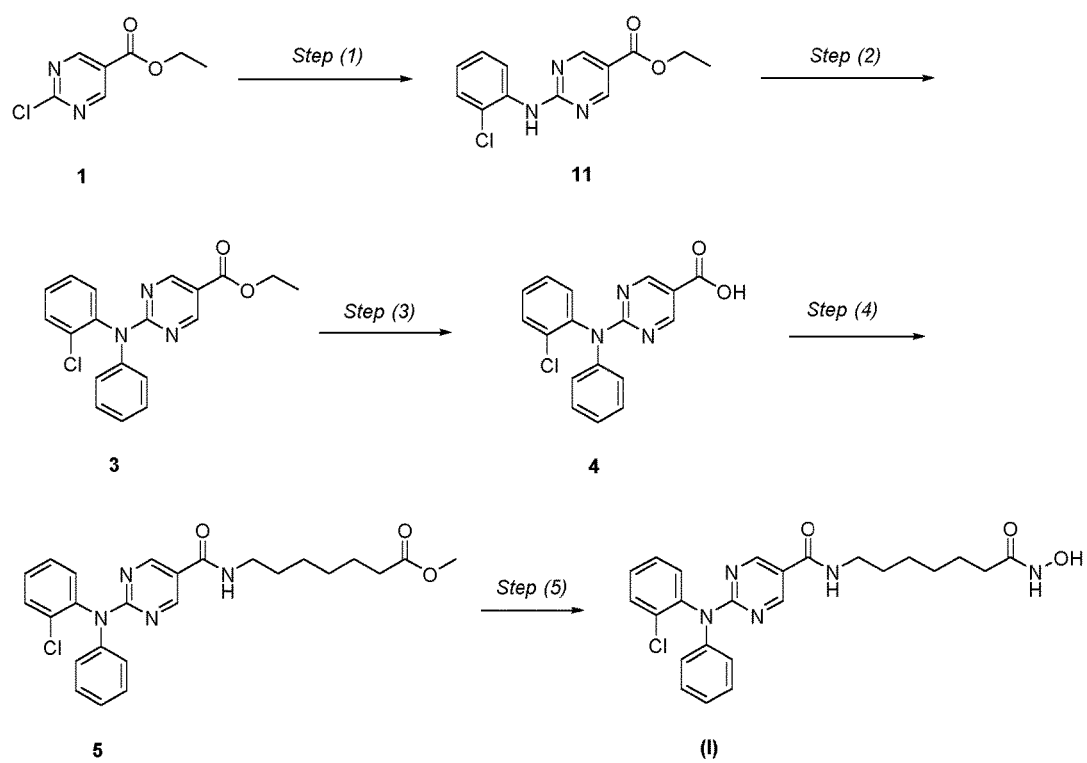
FIG. 2 depicts a specific synthesis of compound (I) according to the improved method described herein.

With reference to FIG. 2, provided herein is a method of making compound (I). In one embodiment, the method comprises the step of converting compound 1 to compound 11, i.e., Step (1). In a particular embodiment, Step (1) comprises reacting ethyl 2-chloropyrimidine-5-carboxylate with 2-chloroaniline. In another embodiment, Step (1) comprises the use of an alcohol solvent (particularly, e.g., ethanol). In another embodiment, Step (1) comprises the use of elevated temperatures (particularly, e.g., about 78° C.). In another particular embodiment, Step (1) comprises the conditions disclosed in Example 4. In another particular embodiment, Step (1) comprises the conditions disclosed in Example 5. In still another embodiment, Step (1) produces compound 11 in at least about 81% yield (e.g., in about 81% yield).

In another embodiment, the method comprises the step of converting compound 11 to compound 3, i.e., Step (2). In another embodiment, Step (2) comprises the use of a polar aprotic solvent (particularly, e.g., dimethylsulfoxide). In another embodiment, Step (2) comprises the use of elevated temperatures (particularly, e.g., about 120±5° C.). In a particular embodiment, Step (2) comprises reacting compound 11 with iodobenzene. In another particular embodiment, Step (2) comprises reacting compound 11 with iodobenzene in presence of copper. In still another particular embodiment, Step (2) comprises reacting compound 11 with iodobenzene in presence of copper and potassium carbonate. In another embodiment, Step (2) comprises the conditions disclosed in Example 4. In another particular embodiment, Step (2) comprises the conditions disclosed in Example 5.

In another embodiment, the method comprises Steps (1)-(2), and the step of converting compound 3 to compound 4, i.e., Step (3). In a particular embodiment, Step (3) comprises forming a mixture of the product of Step (2) (i.e., the reaction mixture comprising compound 3) and water. In another embodiment, Step (3) comprises the use of elevated temperatures (particularly, e.g., about 90-100° C.). In another particular embodiment, Step (3) comprises the conditions disclosed in Example 4. In another particular embodiment, Step (3) comprises the conditions disclosed in Example 5. In still another embodiment, Steps (2)-(3) produce compound 4 from compound 11 in at least about 65% yield (e.g., in about 65% yield). In yet another embodiment, Steps (2)-(3) produce compound 4 from compound 11 in at least about 81% yield (e.g., in about 81% yield).

In another embodiment, the method comprises Steps (1)-(3), and the step of converting compound 4 to compound 5, i.e., Step (4). In another embodiment, Step (3) comprises the use of a polar aprotic solvent (particularly, e.g., dimethylformamide). In a particular embodiment, Step (4) comprises the use of dimethylformamide and dichloromethane. In a particular embodiment, Step (4) comprises reacting compound 4 with methyl 7-aminoheptanoate, or a salt thereof. In another particular embodiment, Step (4) comprises converting compound 4 to an activated acid derivative, then reacting the activated acid derivative with methyl 7-aminoheptanoate. In a particular embodiment, the activated acid derivative is an acid chloride. In another particular embodiment, Step (4) comprises the conditions disclosed in Example 4. In another particular embodiment, Step (4) comprises the conditions disclosed in Example 5.

In another embodiment, the method comprises Steps (1)-(4), and the step of converting compound 5 to compound (I), i.e., Step (5). In another embodiment, Step (5) comprises the use of lowered temperatures (particularly, e.g., about 0-5° C., or about 0-10° C., or about 0±5° C.). In a particular embodiment, Step (5) comprises reacting compound 5 with hydroxylamine, or a salt thereof. In another particular embodiment, Step (5) comprises the use of an alkoxide base in an alcohol solvent (particularly, e.g., sodium methoxide in methanol). In another embodiment, Step (5) comprises crystallizing crude compound (I) from a solvent comprising a C$_1$-C$_6$ alcohol to obtain Form I. In a particular embodiment, the solvent is isopropanol. In another particular embodiment, the solvent is 1-propanol/water. In another particular embodiment, Step (5) comprises the conditions disclosed in Example 4. In another particular embodiment, Step (5) comprises the conditions disclosed in Example 5.

In another embodiment, the method comprises Steps (1)-(5).

In another embodiment, the method comprises Steps (1)-(2), with subsequent steps known in the art, such that compound (I), or a salt thereof, is formed. In another embodiment, the method comprises Steps (1)-(3) with subsequent steps known in the art, such that compound (I), or a salt thereof, is formed. In another embodiment, the method comprises Steps (1)-(4) with subsequent steps known in the art, such that compound (I), or a salt thereof, is formed.

The methods of making compound (I) are superior to previous methods, at least for the following reasons. In contrast to the method of Examples 2 and 3, the claimed methods involve introduction of the chlorine atom in Step (1). This step does not involve conditions under which the aryl chloride is reactive. Accordingly, the chloride moiety is not subject to copper-mediated migration and/or dechlorination. Analysis of Step (1) by high performance liquid chromatography (HPLC) reveals the reaction mixture is free from such migration and/or dechlorination side products.

Compounds and Compositions

Figure 3:
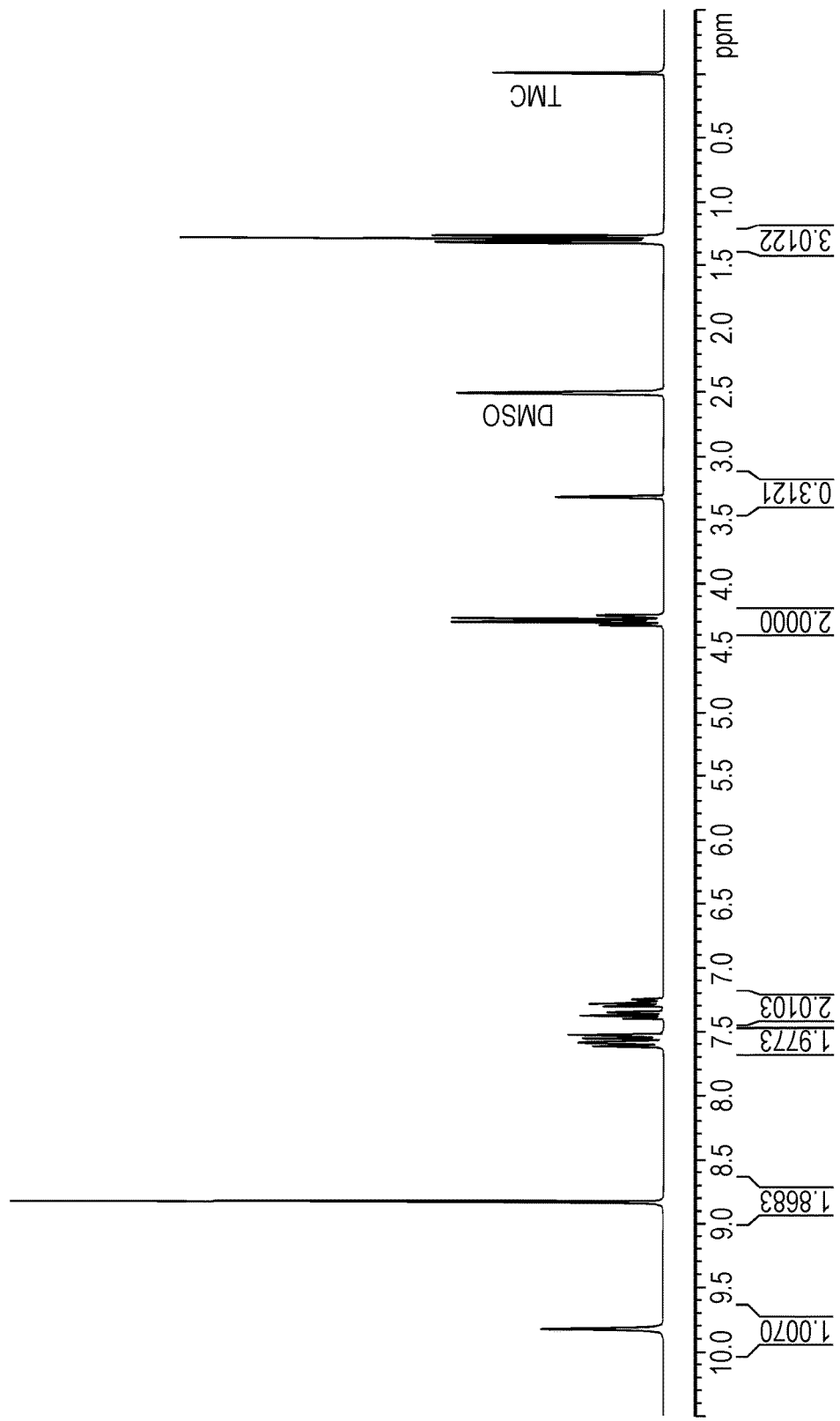
FIG. 3 depicts $^1$HNMR data for compound 11.

With reference to FIGS. 2 and 3, provided herein are compounds useful as intermediates in the synthesis of compound (I). In one aspect, provided herein is the compound 11b, wherein Z is selected from the group consisting of —CN and —CO$_2$R, and wherein R is C$_1$-C$_6$ alkyl. In a particular embodiment, Z is —CO$_2$R. In another particular embodiment, Z is —CO$_2$Et.

In another aspect, provided herein is the compound 11.

Also provided herein are compositions useful in the synthesis of compound (I). In one aspect, provided herein as a composition comprising compounds 1b and 11b, wherein Z is defined according to the embodiments above. In a particular embodiment, Z is —CO$_2$R. In another particular embodiment, Z is —CO$_2$Et. In another embodiment, the composition further comprises 2-chloroaniline.

In another aspect, provided herein is a composition comprising compounds 1 and 11. In one embodiment, the composition further comprises 2-chloroaniline. In another embodiment, the composition further comprises reagents specified in Example 4.

In another aspect, provided herein is a composition comprising compounds 11b and 3b, wherein Z is defined according to the embodiments above. In a particular embodiment, Z is —CO$_2$R. In another particular embodiment, Z is —CO$_2$Et. In one embodiment, the composition further comprises compound 11b. In another embodiment, the composition further comprises iodobenzene. In another embodiment, the composition is free from dechlorination and chlorine-migration impurities, such as de-Cl-3b and m-Cl-3b:

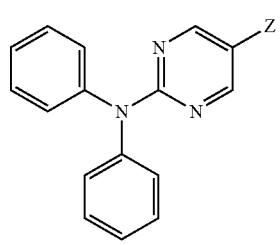
de-Cl-3b

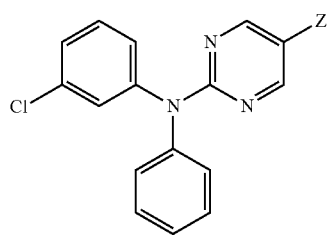
m-Cl-3b wherein Z is defined according to the embodiments above. In another embodiment, the composition further comprises compound 4, or a salt thereof, and is free from dechlorination and chlorine-migration impurities, such as de-Cl-4 and m-Cl-4, or salts thereof:

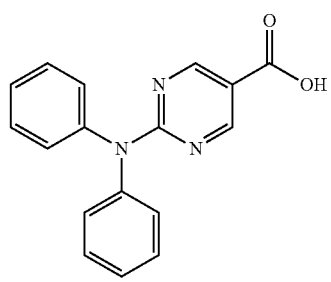
de-Cl-4 m-Cl-4

In another aspect, provided herein is a composition comprising compounds 11 and 3. In one embodiment, the composition further comprises iodobenzene. In another embodiment, the composition is free from dechlorination and chlorine-migration impurities, such as de-Cl-3 and m-Cl-3:

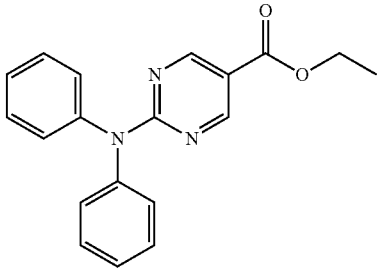
de-Cl-3

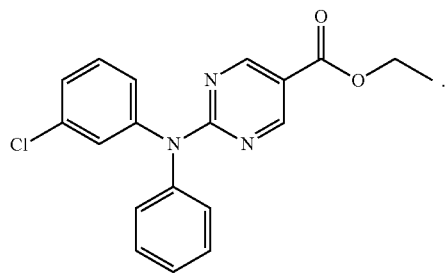

m-Cl-3

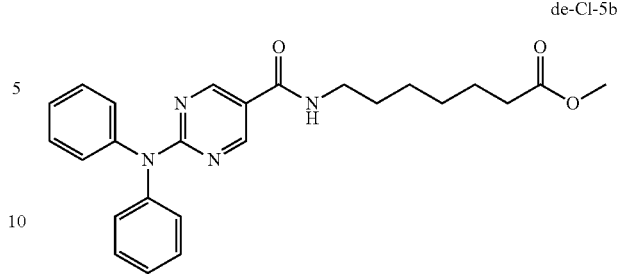

de-Cl-5b m-Cl-5b

In another embodiment, the composition further comprises compound 4, or a salt thereof, and is free from dechlorination and chlorine-migration impurities, such as de-Cl-4 and m-Cl-4, or salts thereof.

In another aspect, provided herein is a composition comprising compound 4 and one or more compounds selected from 1b, 11b and 3b, wherein Z is defined according to the embodiments above. In a particular embodiment, Z is —CO₂R. In another particular embodiment, Z is —CO₂Et.

In another aspect, provided herein is a composition comprising compound 4 and one or more compounds selected from compounds 1, 11 and 3.

In another aspect, provided herein is a composition comprising compound 5b and less than about 1% (combined area percentage as measured by HPLC) of compounds de-Cl-5b and m-Cl-5b:

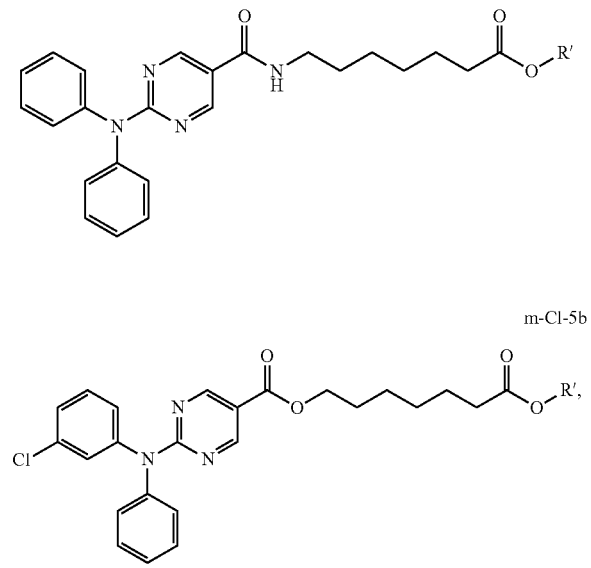

de-Cl-5b m-Cl-5b wherein R' is defined according to the embodiments above. In one embodiment, the composition is free from de-Cl-5b and m-Cl-5b.

In another aspect, provided herein is a composition comprising compound 5 and less than about 1% (combined area percentage as measured by HPLC) of compounds de-Cl-5 and m-Cl-5:

In one embodiment, the composition is free from de-Cl-5 and m-Cl-5.

In another aspect, provided herein is a composition comprising compound 5, compound (I) and less than about 1% (combined area percentage as measured by HPLC) of compounds de-Cl-(I) and m-Cl-(I):

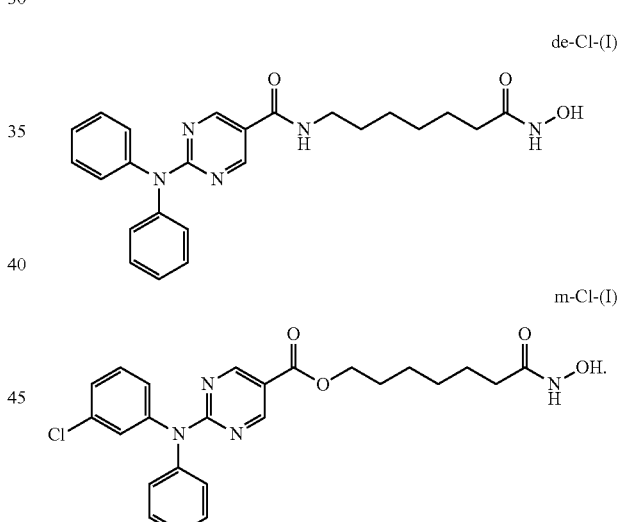

de-Cl-(I)

m-Cl-(I)

In one embodiment, the composition is free from de-Cl-(I) and m-Cl-(I).

DEFINITIONS

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

As used herein, the term "alkyl" refers to a fully saturated branched or unbranched hydrocarbon moiety. Preferably the alkyl comprises 1 to 6 carbon atoms (i.e., $C_1$-$C_6$ alkyl).

As used herein, the term "react" or "reacting" refers to the formation of a bond between two or more reactant compounds to produce a product compound. For example, a first compound and a second compound may react to form a product compound, wherein the product compound comprises a portion of the first compound and a portion of the second compound, wherein the two portions are joined by a covalent bond. The term "reacting" does not refer to the interaction of solvents, catalysts, ligands, or other components that may serve to promote the occurrence of the reaction between the compounds.

As used herein, the terms "salt thereof" or "salts thereof" may refer to acid addition salts, metal salts, or ammonium salts. Such salts can be formed by procedures well known and described in the art. Acid addition salts may be formed from inorganic acids, e.g. hydrochloric, hydrobromic, sulphuric or phosphoric acids, and organic acids, e.g. succinic, malaeic, tartaric, acetic, oxalic or fumaric acid. Examples of addition salts include, without limitation, the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Metal salts of a chemical compound of the invention include alkali metal salts, such as the sodium salt of a chemical compound of the invention containing a carboxy group.

As used herein, the term "copper" can refer to Cu(0), Cu(I) or Cu(II). Non-limiting examples of copper include Cu(0) powder, copper-bronze, cupric oxide, cupric chloride, cupric iodide, cuprous chloride, cuprous iodide and other forms or salts of copper that are known by those of skill in the art.

As used herein, the term "activated acid derivative" refers to a derivative of a carboxylic acid that is susceptible to nucleophilic acyl substitution, for example, by virtue of having a leaving group on the carbonyl carbon. Non-limiting examples of activated acid derivatives include acyl halides (also referred to as acid chlorides), carboxylic acid anhydrides (including, for example, mixed carboxylic acid anhydrides), acyl imidazoles (prepared, for example, by reaction of a carboxylic acid with carbonyl diimidazole), and O-acyl isoureas (prepared, for example, by reaction of a carboxylic acid with a carbodiimide reagent such as EDC or DCC).

Compositions and mixtures that are "free from" a particular solute or substance may comprise less than 5% (e.g., less than 4%, less than 3%, less than 2%, less than 1%, less than 0.1% or less than 0.01%) by weight of the solute or substance. In one embodiment, compositions and mixtures that are "free from" a particular solute or substance comprise an amount of the solute or substance that is below the limit of detection of the analytical instrumentation described herein.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the claims.

EXAMPLES

Instrumentation and Methods

Differential Scanning calorimetry (DSC) data were collected using a TA Instruments Q10 DSC. Approximately, samples (2-8 mg) were placed in unsealed but covered hermetic alodined aluminum sample pans and scanned from 30 to 300° C. at a rate of 10° C./min under a nitrogen purge of 50 mL/min.

Thermal Gravimetric Analysis (TGA) data were collected using a TA Instruments TGA Q500. Approximately, 5-10 mg samples were placed in an open, pre-tared aluminum sample pan and scanned from 25 to 300° C. at a rate of 10° C./min using a nitrogen purge at 60 mL/min.

X-ray Powder Diffractometer (XRPD) patterns were obtained using a Bruker D8 Advance equipped with a Cu Kα radiation source ($\lambda=1.54°$ A), a 9-position sample holder and a LYNXEYE super speed detector. Samples were placed on zero-background, silicon plate holders for analysis.

Dynamic Vapor Soprtion (DVS) analysis was performed using an Aquadyne DVS-2 gravimetric water sorption analyzer. The relative humidity was adjusted between 2-95% and the weight of the sample was continuously monitored and recorded with respect to the relative humidity and time.

Proton Nuclear Magnetic Resonance ($^1$H-NMR): Samples were prepared by dissolving the compound in deuterated dimethylsulfoxide with 0.05% (v/v) tetramethylsilane (TMS). Spectra were collected at ambient temperature on a Bruker Avance 300 MHz NMR equipped with TopSpin software. The number of scans was 16 for $^1$H-NMR.

Karl Fischer (KF): The apparent water content in samples was determined by Karl Fischer titration using a Mettler Toledo DL39 Coulometric KF Titrator. HYDRANAL-Coulomat AD was used as the titrant. About 20 mg of the solid was used for titration. The analytical parameters are presented in Table 1.

TABLE 1

| KF Parameter | Value |
| --- | --- |
| Speed [%] | 40 |
| Mix time [sec] | 10 |
| Auto start | No |
| Blank [µg] | 0 |
| Drift [µg/min] | 5 |
| Calculation | Ug |
| Standby | Yes |
| Initial drift [µg/min] | <10 |
| Initial Potential [mV] | 100 |

Example 1: Comparative Synthesis of 2-(diphenylamino)-N-(7-(hydroxyamino)-7-oxoheptyl)pyrimidine-5-carboxamide Reaction Scheme

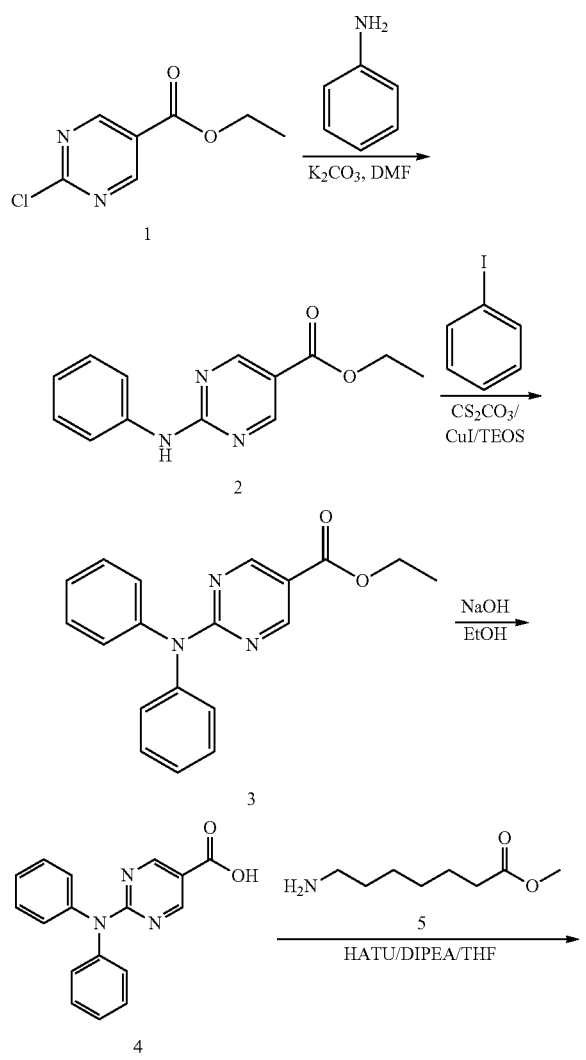

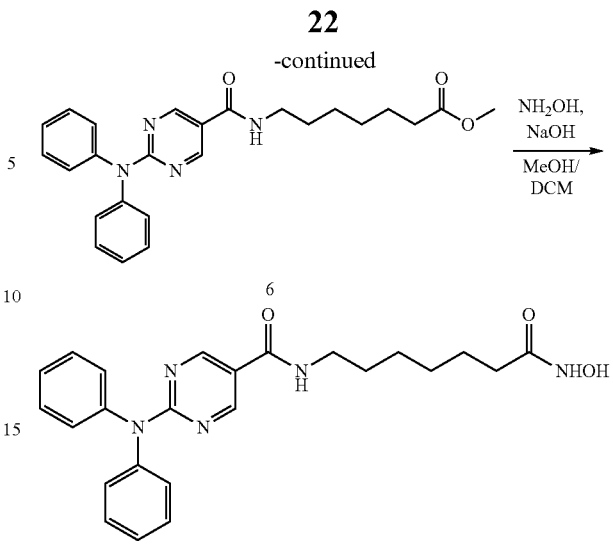

Synthesis of Intermediate 2

A mixture of aniline (3.7 g, 40 mmol), compound 1 (7.5 g, 40 mmol), and $K_2CO_3$ (11 g, 80 mmol) in DMF (100 ml) was degassed and stirred at 120° C. under $N_2$ overnight. The reaction mixture was cooled to r.t. and diluted with EtOAc (200 ml), then washed with saturated brine (200 ml×3). The organic layers were separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3

A mixture of compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4

2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over $Na_2SO_4$. Removal of the solvent gave a brown solid (2.5 g, 92%).

Synthesis of Intermediate 6

A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 2: Comparative Synthesis of 2-((2-chlorophenyl)(phenyl)amino)-N-(7-(hydroxyamino)-7-oxoheptyl)pyrimidine-5-carboxamide—Compound (I)

Reaction Scheme

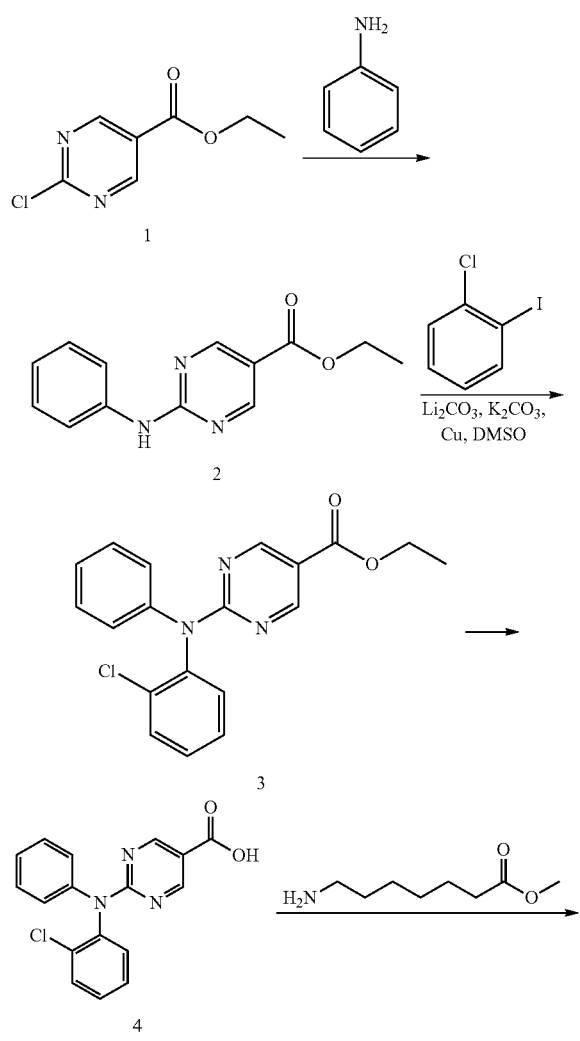

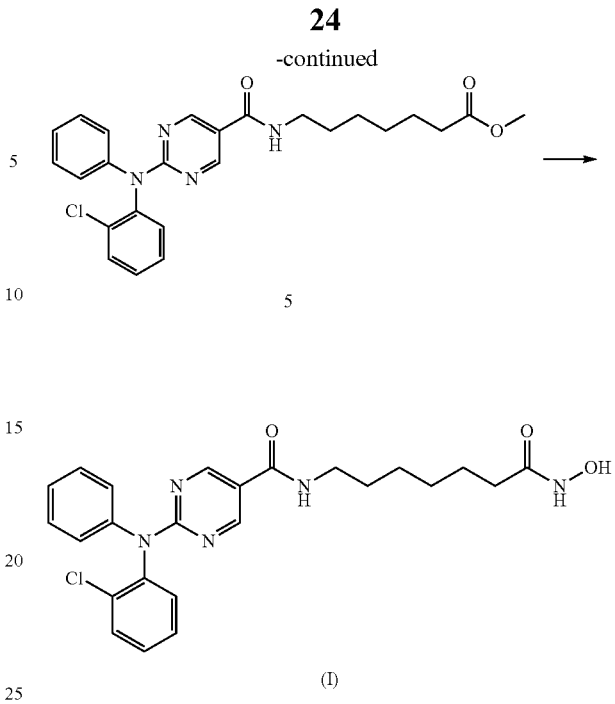

Step (1)

Synthesis of Intermediate 2

A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Step (2)

Synthesis of Intermediate 3

A mixture of compound 2 (69.2 g, 1 equiv.), 1-chloro-2-iodobenzene (135.7 g, 2 equiv.), $Li_2CO_3$ (42.04 g, 2 equiv.), $K_2CO_3$ (39.32 g, 1 equiv.), Cu (1 equiv. 45 μm) in DMSO (690 ml) was degassed and purged with nitrogen. The resulting mixture was stirred at 140° C. for 36 hours. Work-up of the reaction gave compound 3 at 93% yield.

Step (3)

Synthesis of Intermediate 4

2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Step (4)

Synthesis of Intermediate 5

A procedure analogous to the Synthesis of Intermediate 6 in Example 1 was used.

Step (5)

Synthesis of 2-((2-chlorophenyl)(phenyl)amino)-N-(7-(hydroxyamino)-7-oxoheptyl)pyrimidine-5-carboxamide A procedure analogous to the Synthesis of 2-(diphenylamino)-N-(7-(hydroxyamino)-7-oxoheptyl)pyrimidine-5-carboxamide in Example 1 was used.

Example 3: Process Development for Steps 2-3 of Example 2

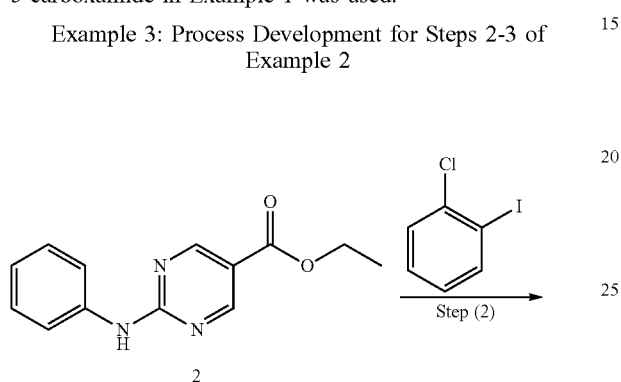

TABLE 2

| | | Reactants and reagents | | | | |
|---|---|---|---|---|---|---|
| No. | Cpd 2 | 2-Cl-iodo-benzene | Solvent | Base | Catalyst | Temp. (° C.) |
| 1 | 2.43 g (1.0 eq) | 4.77 g (2.0 eq) | 25 mL | $Li_2CO_3$ (2.22 g, 3 eq) | Cu (1.0 eq, 106 μm) | 130° C. |
| 2 | 24.3 g (1.0 eq) | 47.7 g (2.0 eq) | 240 mL | $Li_2CO_3$ (22.2 g, 3 eq) | Cu (1.0 eq, 106 μm) | 130-150° C. |
| 3 | 24.3 g (1.0 eq) | 47.7 g (2.0 eq) | 240 mL | $Li_2CO_3$ (22.2 g, 3 eq) | Cu (1.0 eq, 106 μm) | 150° C. |
| 4 | 24.3 g (1.0 eq) | 47.7 g (2.0 eq) | 150 mL | $Li_2CO_3$ (22.2 g, 3 eq); after 42 h, $K_2CO_3$ (13.8, 1 eq) | Cu (1.0 eq, 45 μm) | 150° C. |
| 5 | 24.3 g (1.0 eq) | 47.7 g (2.0 eq) | 240 mL | $Li_2CO_3$ (22.2 g, 2 eq) $K_2CO_3$ (19.65, 1 eq) | Cu (1.0 eq, 45 μm) | 140° C. |
| 6 | 69.2 g (1.0 eq) | 135.7 g (2.0 eq) | 690 mL | $Li_2CO_3$ (42.04 g, 2 eq) $K_2CO_3$ (39.32 g, 1 eq) | Cu (1.0 eq, 45 μm) | 140° C. |

TABLE 3

| No. | Conversion (%) | m-Cl 3/4 | de-Cl 3/4 |
|---|---|---|---|
| 1 | 91.7% | 1.43% | — |
| 2 | 84.2% | 1.92% | — |
| 3 | 70.6% | 2.19% | — |
| 4 | 94.4% | 7.88% | 3.0% |
| 5 | 89.4% | 7.63% | 1.08% |
| 6 | 93% | 8.5% | 1.6% |

TABLE 4

Purification of Compound 4 by extraction and slurry

| Purification Conditions | de-Cl-4 | m-Cl-4 | Compound 4 HPLC |
|---|---|---|---|
| Crude Product | 3.69% | 3.53% | 89.53% |
| MTBE/Heptane (5 vol/15 vol) | 2.93% | 2.57% | 93.34% |
| iPrOH/H$_2$O (1 vol/2 vol) | 3.55% | 3.27% | 91.41% |
| EtOAc/PE (10 vol/10 vol) | 3.87% | 1.43% | 93.48% |
| MTBE/Heptane (10 vol/10 vol) | 2.83% | 2.67% | 92.57% |
| MEK/Heptane (3 vol/6 vol) | 4.42% | 3.16% | 90.00% |
| EtoAc | 3.87% | 1.43% | 93.48% |
| iProAc | 3.91% | 2.81% | 90.91% |

Example 4: Improved Synthesis of Compound (I)

Reaction Scheme

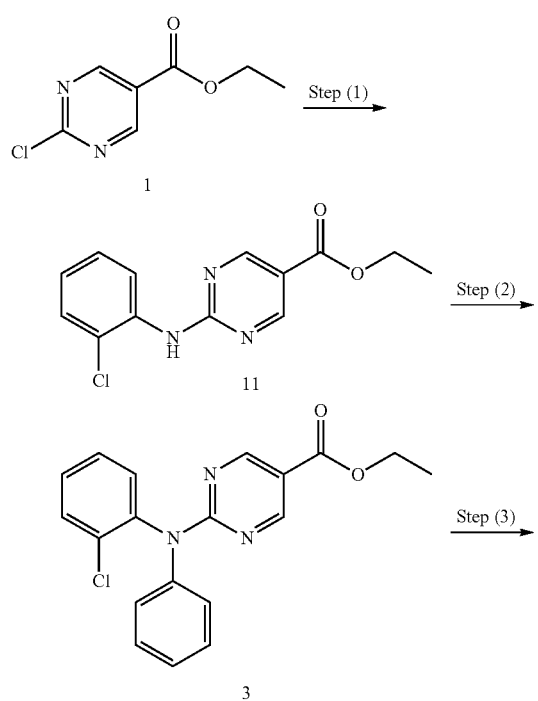

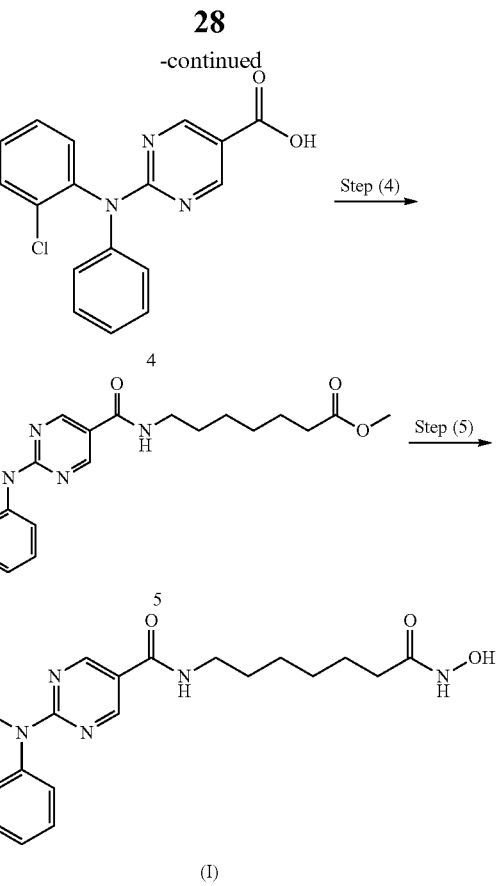

Step (1)

Synthesis of Compound 11

Ethyl 2-chloropyrimidine-5-carboxylate (ACY-5, 7.0 Kgs), ethanol (60 Kgs), 2-Chloroaniline (9.5 Kgs, 2 eq) and acetic acid (3.7 Kgs, 1.6 eq) were charged to a reactor under inert atmosphere. The mixture was heated to reflux. After at least 5 hours the reaction was sampled for HPLC analysis (method TM-113.1016). When analysis indicated reaction completion (<1% ACY-5), the mixture was cooled to 70±5° C. and N,N-Diisopropylethylamine (DIPEA) was added. The reaction was then cooled to 20±5° C. and the mixture was stirred for an additional 2-6 hours. The resulting precipitate is filtered and washed with ethanol (2×6 Kgs) and heptane (24 Kgs). The cake is dried under reduced pressure at 50±5° C. to a constant weight to produce 8.4 Kgs compound 11 (81% yield and 99.9% purity (method TM-113.1016)). See $^1$HNMR data in FIG. 3.

Step (2)

Synthesis of Compound 3

Copper powder (0.68 Kgs, 1 eq, <75 micron), potassium carbonate (4.3 Kgs, 3.0 eq), and dimethyl sulfoxide (DMSO, 12.3 Kgs) were added to a reactor (vessel A). The resulting solution was heated to 120±5° C. In a separate reactor (vessel B), a solution of compound 11 (2.9 Kgs) and iodobenzene (4.3 Kgs, 2 eq) in DMSO (5.6 Kgs) was heated at 40±5° C. The mixture was then transferred to vessel A over 2-3 hours. The reaction mixture was heated at 120±5° C. for 8-24 hours, until HPLC analysis (method TM-113.942) determined that ≤1% compound 11 was remaining.

Step (3)

Synthesis of Compound 4

Figure 4:
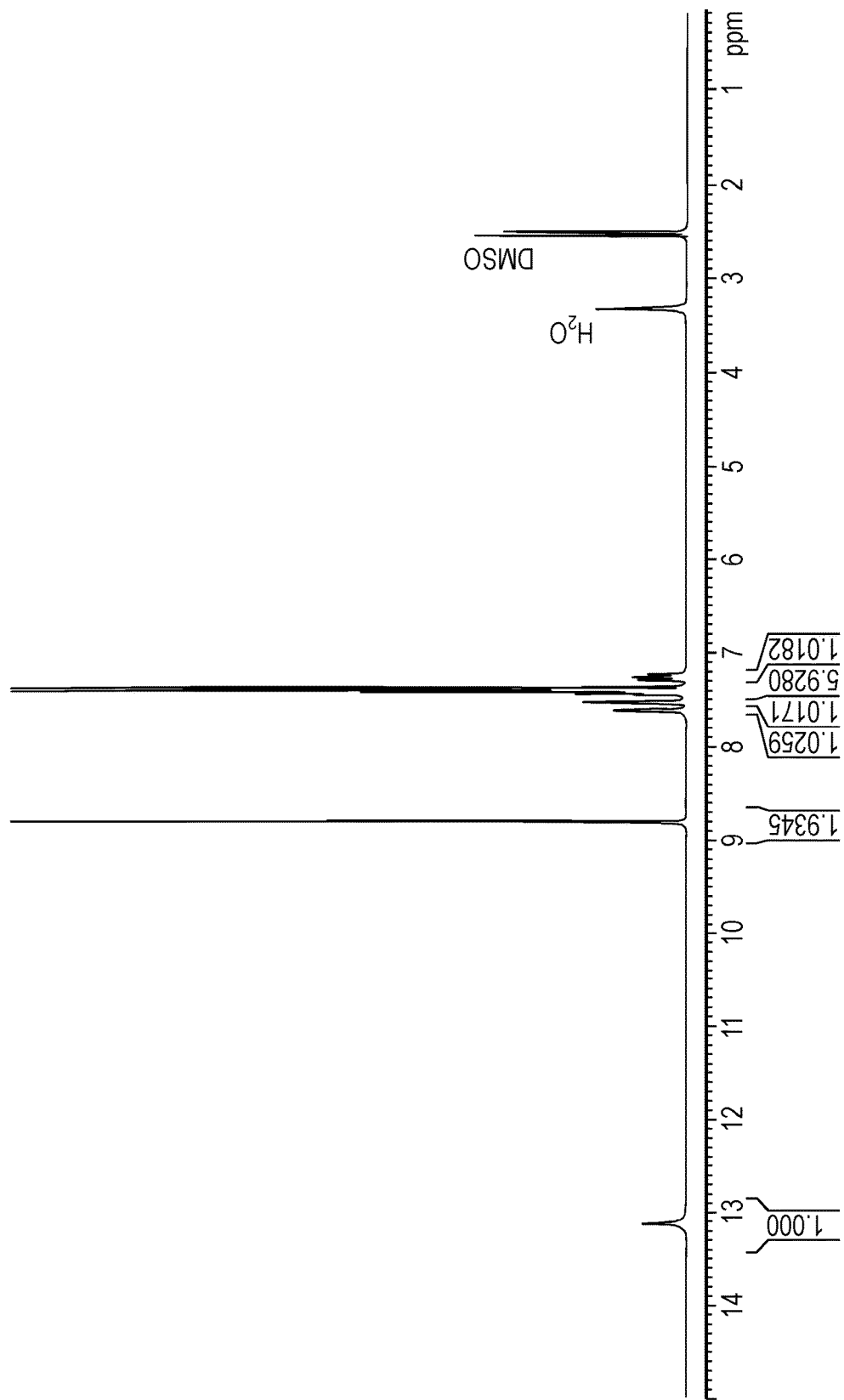
FIG. 4 depicts $^1$HNMR data for compound 4.

The mixture of Step (2) was cooled to 90-100° C. and purified water (59 Kgs) was added. The reaction mixture was stirred at 90-100° C. for 2-8 hours until HPLC (method TM-113.942-see step 2) showed that ≤1% compound 3 was remaining. The reactor was cooled to 25° C. The reaction mixture was filtered through Celite, then a 0.2 micron filter, and the filtrate was collected. The filtrate was extracted with methyl t-butyl ether twice (2×12.8 Kgs). The aqueous layer was cooled to 0-5° C., then acidified with 6N hydrochloric acid (HCl) to pH 2-3 while keeping the temperature <25° C. The reaction was then cooled to 5-15° C. The precipitate was filtered and washed with cold water. The cake was dried at 45-55° C. under reduced pressure to constant weight to obtain 2.2 kg (65% yield) compound 4 in 90.3% AUC purity (method TM-113.942-see step 2). No dechlorinated product or Cl-migration product (i.e., de-Cl-4 or m-Cl-4) was observed. See $^1$HNMR data in FIG. 4.

Step (4)

Synthesis of Compound 5

Dichloromethane (40.3 Kgs), DMF (33 g, 0.04 eq) and compound 4 (2.3 Kg) were charged to a reaction flask. The solution was filtered through a 0.2 μm filter and was returned to the flask. Oxalyl chloride (0.9 Kgs, 1 eq) was added via addition funnel over 30-120 minutes at <30° C. The batch was then stirred at <30° C. until reaction completion (compound 4≤3%) was confirmed by HPLC (method TM-113.946). Next, the dichloromethane solution was concentrated and residual oxalyl chloride was removed under reduced pressure at <40° C. When HPLC analysis (method TM-113.946) indicated that <0.10% oxalyl chloride was remaining, the concentrate was dissolved in fresh dichloromethane (24 Kgs) and transferred back to the reaction vessel (Vessel A).

Figure 5:
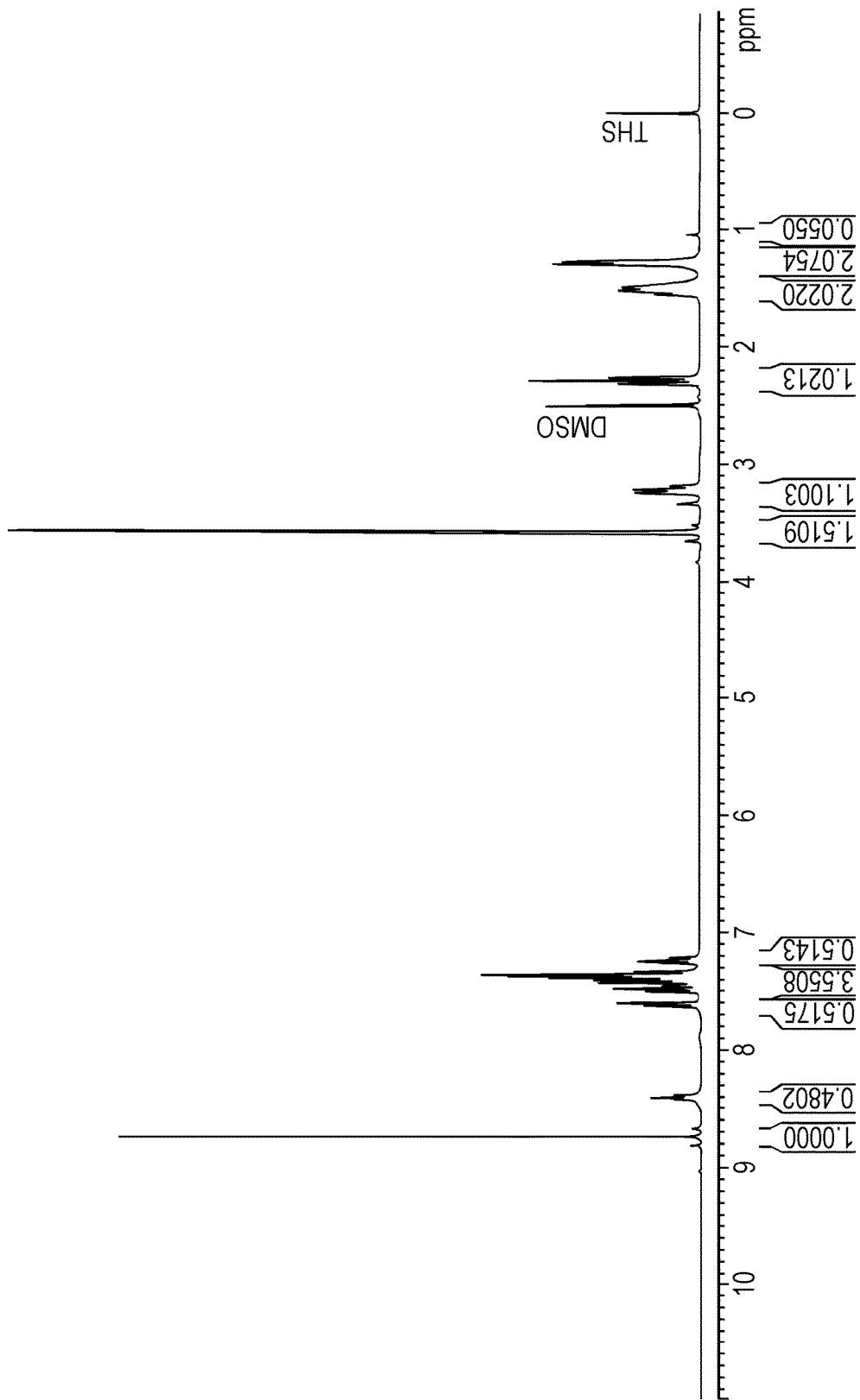
FIG. 5 depicts $^1$HNMR data for compound 5.

A second vessel (Vessel B) was charged with Methyl 7-aminoheptanoate hydrochloride (Compound A1, 1.5 Kgs, 1.09 eq), DIPEA (2.5 Kgs, 2.7 eq), 4 (Dimethylamino) pyridine (DMAP, 42 g, 0.05 eq), and DCM (47.6 Kgs). The mixture was cooled to 0-10° C. and the acid chloride solution in Vessel A was transferred to Vessel B while maintaining the temperature at 5° C. to 10° C. The reaction is stirred at 5-10° C. for 3 to 24 hours at which point HPLC analysis indicated reaction completion (method TM-113.946, compound 4≤5%). The mixture was then extracted with a 1M HCl solution (20 Kgs), purified water (20 Kgs), 7% sodium bicarbonate (20 Kgs), purified water (20 Kgs), and 25% sodium chloride solution (20 Kgs). The dichloromethane was then vacuumdistilled at <40° C. and chased repeatedly with isopropyl alcohol. When analysis indicated that <1 mol % DCM was remaining, the mixture was gradually cooled to 0-5° C. and was stirred at 0-5° C. for an at least 2 hours. The resulting precipitate was collected by filtration and washed with cold isopropyl alcohol (6.4 Kgs). The cake was sucked dry on the filter for 4-24 hours, then was further dried at 45-55° C. under reduced pressure to constant weight. 2.2 Kgs (77% yield) was isolated in 95.9% AUC purity (method TM-113.953) and 99.9 wt %. See $^1$HNMR data in FIG. 5.

Step (5)

Synthesis of Compound (I)

Hydroxylamine hydrochloride (3.3 Kgs, 10 eq) and methanol (9.6 Kgs) were charged to a reactor. The resulting solution was cooled to 0-5° C. and 25% sodium methoxide (11.2 Kgs, 11 eq) was charged slowly, maintaining the temperature at 0-10° C. Once the addition was complete, the reaction was mixed at 20° C. for 1-3 hours and filtered, and the filter cake was washed with methanol (2×2.1 Kgs). The filtrate (hydroxylamine free base) was returned to the reactor and cooled to 0±5° C. Compound 5 (2.2 Kgs) was added. The reaction was stirred until the reaction was complete (method TM-113.964, compound 5≤2%). The mixture was filtered and water (28 Kgs) and ethyl acetate (8.9 Kgs) were added to the filtrate. The pH was adjusted to 8-9 using 6N HCl then stirred for up to 3 hours before filtering. The filter cake was washed with cold water (25.7 Kgs), then dried under reduced pressure to constant weight. The crude solid compound (I) was determined to be Form IV/Pattern D.

Figure 6:
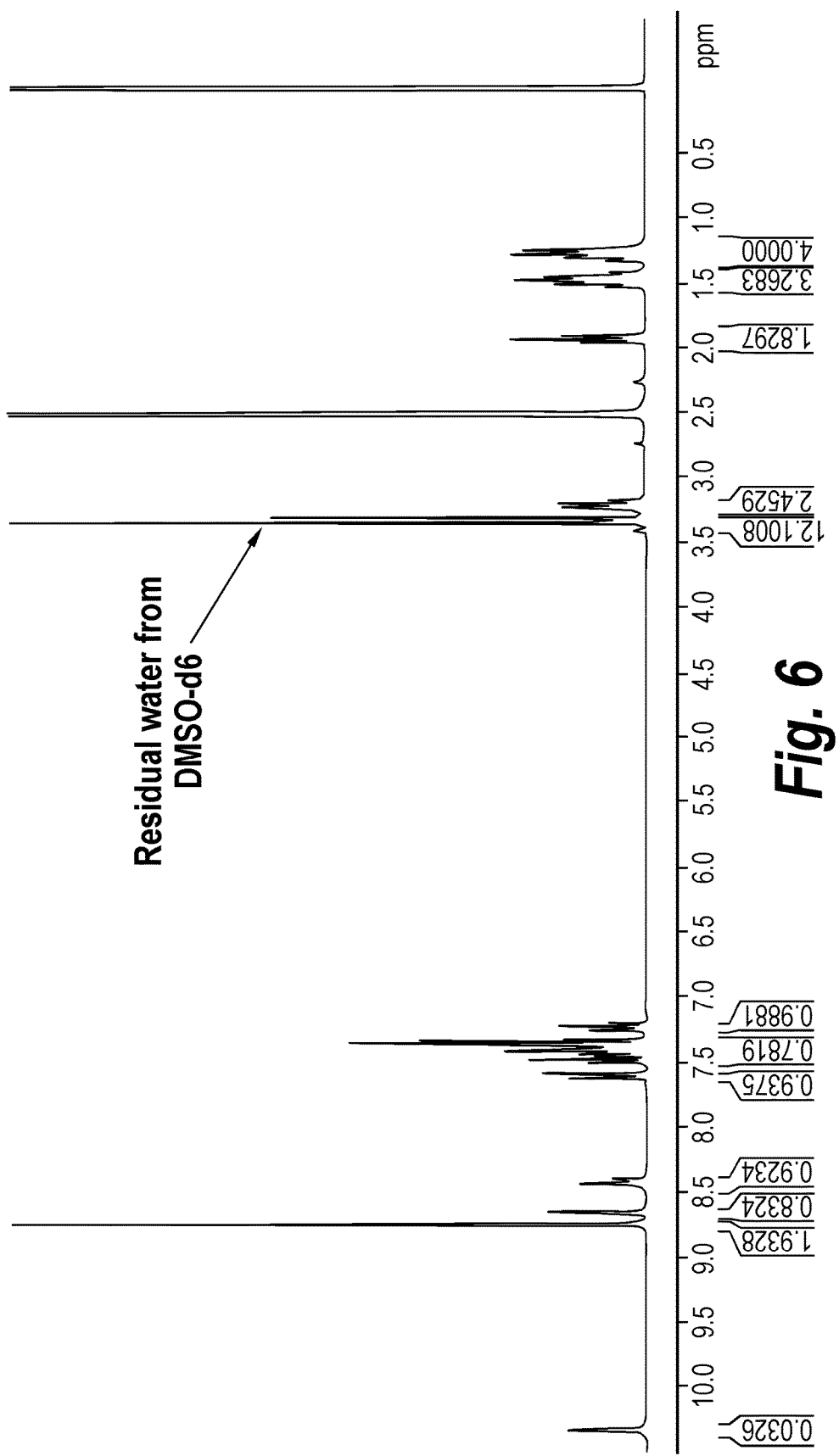
FIG. 6 depicts $^1$HNMR data for compound (I).
Figure 7:
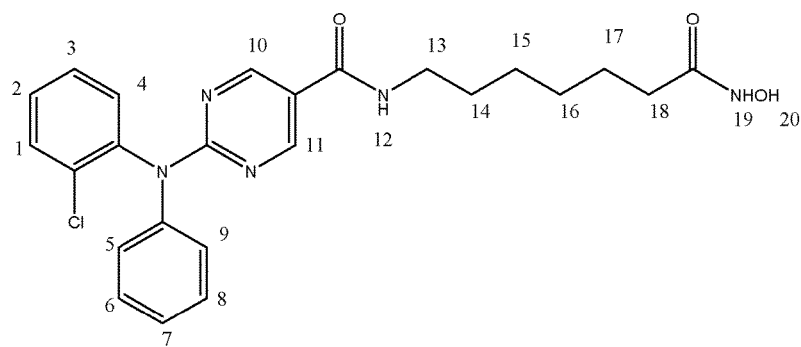
FIG. 7 depicts the correlation of $^1$HNMR data to the structure of compound (I).

The crude solid (1.87 Kgs) was suspended in isopropyl alcohol (IPA, 27.1 Kg). The slurry was heated to 75±5° C. to dissolve the solids. The solution was seeded with crystals of Compound (I) (Form I/Pattern A), and was allowed to cool to ambient temperature. The resulting precipitate was stirred for 1-2 hours before filtering. The filter cake was rinsed with IPA (2×9.5 Kgs), then dried at 45-55° C. to constant weight under reduced pressure to result in 1.86 kg crystalline white solid Compound (I) (Form I/Pattern A) in 85% yield and 99.5% purity. See $^1$HNMR data in FIG. 6.

Example 5: Alternative Synthesis of Compound (I)

Reaction Scheme

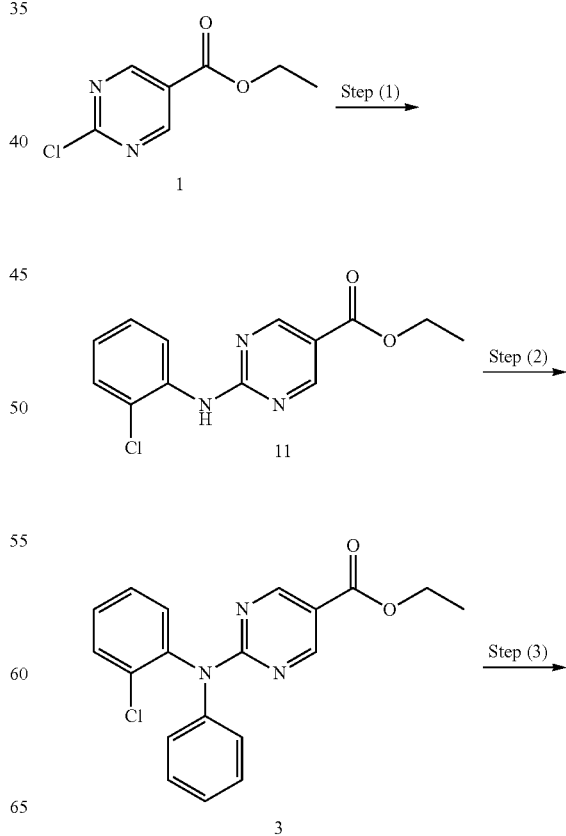

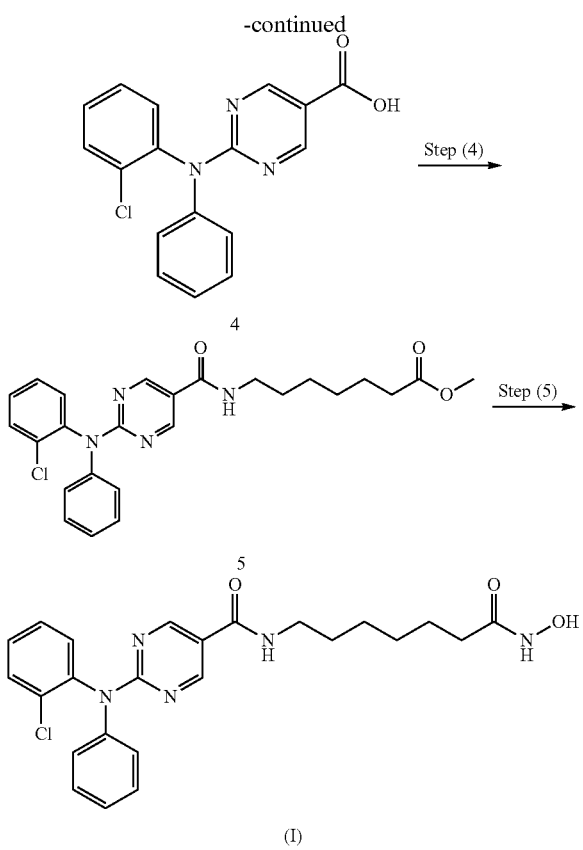

Step (1)

Synthesis of Compound 11

Ethyl 2-chloropyrimidine-5-carboxylate (ACY-5, 250 g), ethanol (2179 g), 2-Chloroaniline (339.3 g, 2 eq) and acetic acid (132.1 g, 1.6 eq) were charged to a reactor under inert atmosphere. The mixture was heated to reflux. After at least 5 hours the reaction was sampled for HPLC analysis. When analysis indicated reaction completion (<1% ACY-5), the mixture was cooled to 70±5° C. and N,N-Diisopropylethylamine (DIPEA, 553.6 g, 3.2 eq) was added. The reaction was then cooled to 20±5° C. and the mixture was stirred for an additional 2-6 hours. The resulting precipitate is filtered and washed with ethanol (2×401 g) and heptane (2×428 g). The cake is dried under reduced pressure at 50±5° C. to a constant weight to produce 307.1 g compound 11 (82.5% yield and 99.7% purity.

Step (2)

Synthesis of Compound 3

Cuprous iodide (17.5 g, 8 eq), potassium carbonate (373.8 g, 3 eq), L-Prolin (11.4 g, 0.11 eq.) and dimethyl sulfoxide (DMSO, and 1180 g) were added to a reactor (vessel A). The resulting solution was heated to 90±5° C. In a separate reactor (vessel B), a solution of compound 11 (250 g) and iodobenzene (1469.5 g, 8 eq) in DMSO (402.5 g) was heated at 40±5° C. The mixture was then transferred to vessel A over 2-3 hours. The reaction mixture was heated at 90±5° C. for 8-24 hours, until HPLC analysis determined that ≤1% compound 11 was remaining.

Step (3)

Synthesis of Compound 4

The mixture of Step (2) was cooled to 40-50° C. and water (500 g) and potassium hydroxide solution 10% (700.0 g, 2.8 eq) were added. The reaction mixture was stirred at 40-50° C. for 2-8 hours until HPLC showed that ≤1% compound 3 was remaining. The reactor was cooled to 25° C. The reaction mixture was filtered through Celite, then a 0.2 micron filter, and the filtrate was collected. The filtrate was extracted with toluene (3×150 g). The aqueous layer was cooled to 0-5° C., then acidified with hydrochloric acid (HCl) to pH 2-3 while keeping the temperature <25° C. The reaction was then cooled to 5-15° C. The precipitate was filtered and washed with cold water. The cake was dried at 45-55° C. under reduced pressure to constant weight to obtain 291 g (81% yield) compound 4 in 98% AUC purity. No dechlorinated product or Cl-migration product (i.e., de-Cl-4 or m-Cl-4) was observed.

Step (4)

Synthesis of Compound 5

Compound 4 (250.0 g), A-1 (159.2 g, 1.06 eq) and Methy-THF (5113 g) were charged to the reactor. DIPEA (283.7 g, 2.85 eq), hydroxybenzotriazole (HOBt, 12.5 g, 0.11 eq) and 1-ethyl-3-(3-dimethylaminopropyl)carbodiimide (EDC.HCl, 216.3 g, 1.47 eq) were added. The reaction solution was stirred at ambient temperature for 6-24 hours, at which point HPLC analysis indicated reaction completion (compound 4≤3%). The mixture was then extracted with a 1M HCl solution (2270 g), purified water (2270 g), 7% sodium bicarbonate (2270 g), purified water (2270 g), and 25% sodium chloride solution (2270 g). The Methyl-THF was then vacuumdistilled at <40° C. and chased repeatedly with isopropyl alcohol. When analysis indicated that <1 mol % methyl-THF was remaining, the mixture was gradually cooled to 0-5° C. and was stirred at 0-5° C. for an at least 2 hours. The resulting precipitate was collected by filtration and washed with cold isopropyl alcohol (700 g). The cake was sucked dry on the filter for 4-24 hours, then was further dried at 45-55° C. under reduced pressure to constant weight. 294 g (82% yield) was isolated in 99.6% AUC purity and 99.4 wt %.

Step (5)

Synthesis of Compound (I)

Hydroxylamine hydrochloride (330 g, 10 eq) and methanol (960 g) were charged to a reactor. The resulting solution was cooled to 0-5° C. and 25% sodium methoxide (1120 g, 11 eq) was charged slowly, maintaining the temperature at 0-10° C. Once the addition was complete, the reaction was mixed at 20° C. for 1-3 hours and filtered, and the filter cake was washed with methanol (2×210 g). The filtrate (hydroxylamine free base) was returned to the reactor and cooled to 0±5° C. Compound 5 (220 g) was added. The reaction was stirred until the reaction was complete (compound 5≤2%). The mixture was filtered and water (280 g) and ethyl acetate (890 g) were added to the filtrate. The pH was adjusted to 8-9 using HCl then stirred for up to 3 hours before filtering. The filter cake was washed with cold water (2570 g), then dried under reduced pressure to constant weight to yield 980 g crude solid in 83% yield. The crude solid compound (I) was determined to be Form IV/Pattern D.

The crude solid (980 g) was suspended in 1-propanol (400 g) and purified water (220 g). The suspension was heated to 40° C. The batch was then cooled to 38° C. over 30 minutes.

The solution was seeded with crystals of Compound (I) (Form I/Pattern A, 2-5 wt %). The batch was kept at 37-38° C. for 2-4 hours, then was gradually cooled to 20±2° C. Water (950 g) was charged over 3-5 hours. The batch was cooled to 12° C. and was stirred for 2 hrs at this temperature. The batch was filtered and washed with cold 1-propanol/water, then dried at 50±5° C. to constant weight to yield 910 g purified compound (I) in 93% yield and 99.8% AUC purity.

HPLC Methods

I. Method 113.1016

| Column | Zorbax Eclipse XDB-C18, 4.6 mm × 150 mm, 3.5 μm |
|---|---|
| Column Temperature | 40° C. |
| UV Detection Wavelength | Bandwidth 4 nm, Reference off, 215 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| | Time (min) | Mobile Phase A | Mobile Phase B |
|---|---|---|---|
| Gradient | 0.0 | 98% | 2% |
| | 36.0 | 0% | 100% |
| | 40.0 | 0% | 100% |
| | 40.1 | 98% | 2% |
| | 46.0 | 98% | 2% |

II. Method 113.942

| Column | ACE Excel 3 super C18, 4.6 mm × 150 mm, 3 μm |
|---|---|
| Column Temperature | 40° C. |
| UV Detection Wavelength | Bandwidth 4 nm, Reference off, 214 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 22.0 min |
| Run Time | 28.0 min |

| | Time (min) | Mobile Phase A | Mobile Phase B |
|---|---|---|---|
| Gradient | 0.0 | 98% | 2% |
| | 18.0 | 0% | 100% |
| | 22.0 | 0% | 100% |
| | 22.1 | 98% | 2% |
| | 28.0 | 98% | 2% |

III. Method 113.953

| Column | ACE Excel 3 super C18, 4.6 mm × 150 mm, 3 μm |
|---|---|
| Column Temperature | 40° C. |
| UV Detection Wavelength | Bandwidth 4 nm, Reference off, 235 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| | Time (min) | Mobile Phase A | Mobile Phase B |
|---|---|---|---|
| Gradient | 0.0 | 98% | 2% |
| | 36.0 | 0% | 100% |
| | 40.0 | 0% | 100% |
| | 40.1 | 98% | 2% |
| | 46.0 | 98% | 2% |

IV. Method 113.946

| Column | Zorbax Eclipse XDB-C18, 4.6 mm × 150 mm, 3.5 μm |
|---|---|
| Column Temperature | 40° C. |
| UV Detection Wavelength | Bandwidth 4 nm, Reference off, 214 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| | Time (min) | Mobile Phase A | Mobile Phase B |
|---|---|---|---|
| Gradient | 0.0 | 98% | 2% |
| | 36.0 | 0% | 100% |
| | 40.0 | 0% | 100% |
| | 40.1 | 98% | 2% |
| | 46.0 | 98% | 2% |

V. Method 113.964

| Column | ACE Excel 3 super C18, 4.6 mm × 150 mm, 3 μm |
|---|---|
| Column Temperature | 40° C. |
| UV Detection Wavelength | Bandwidth 4 nm, Reference off, 272 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| | Time (min) | Mobile Phase A | Mobile Phase B |
|---|---|---|---|
| Gradient | 0.0 | 98% | 2% |
| | 36.0 | 0% | 100% |
| | 40.0 | 0% | 100% |
| | 40.1 | 98% | 2% |
| | 46.0 | 98% | 2% |

VI. Method 113.941

| Column | Zorbax Eclipse XDB-C18, 4.6 mm × 150 mm, 3.5 μm |
|---|---|
| Column Temperature | 40° C. |
| UV Detection Wavelength | Bandwidth 4 nm, Reference off, 272 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| | Time (min) | Mobile Phase A | Mobile Phase B |
|---|---|---|---|
| Gradient | 0.0 | 98% | 2% |
| | 36.0 | 0% | 100% |
| | 40.0 | 0% | 100% |
| | 40.1 | 98% | 2% |
| | 46.0 | 98% | 2% |

Crystal Forms of Compound (I)

I. Form I/Pattern A 2-((2-chlorophenyl)(phenyl)amino)-N-(7-(hydroxyamino)-7-oxoheptyl)pyrimidine-5-carboxamide (i.e., compound (I)) may exist in crystal Form I (referred to herein as "Form I"). Form I can be characterized using X-ray powder diffraction (XRPD). The XRPD pattern of Form I is shown in FIG. 8, and is referred to as "Pattern A".

TABLE 5

Figure 8:
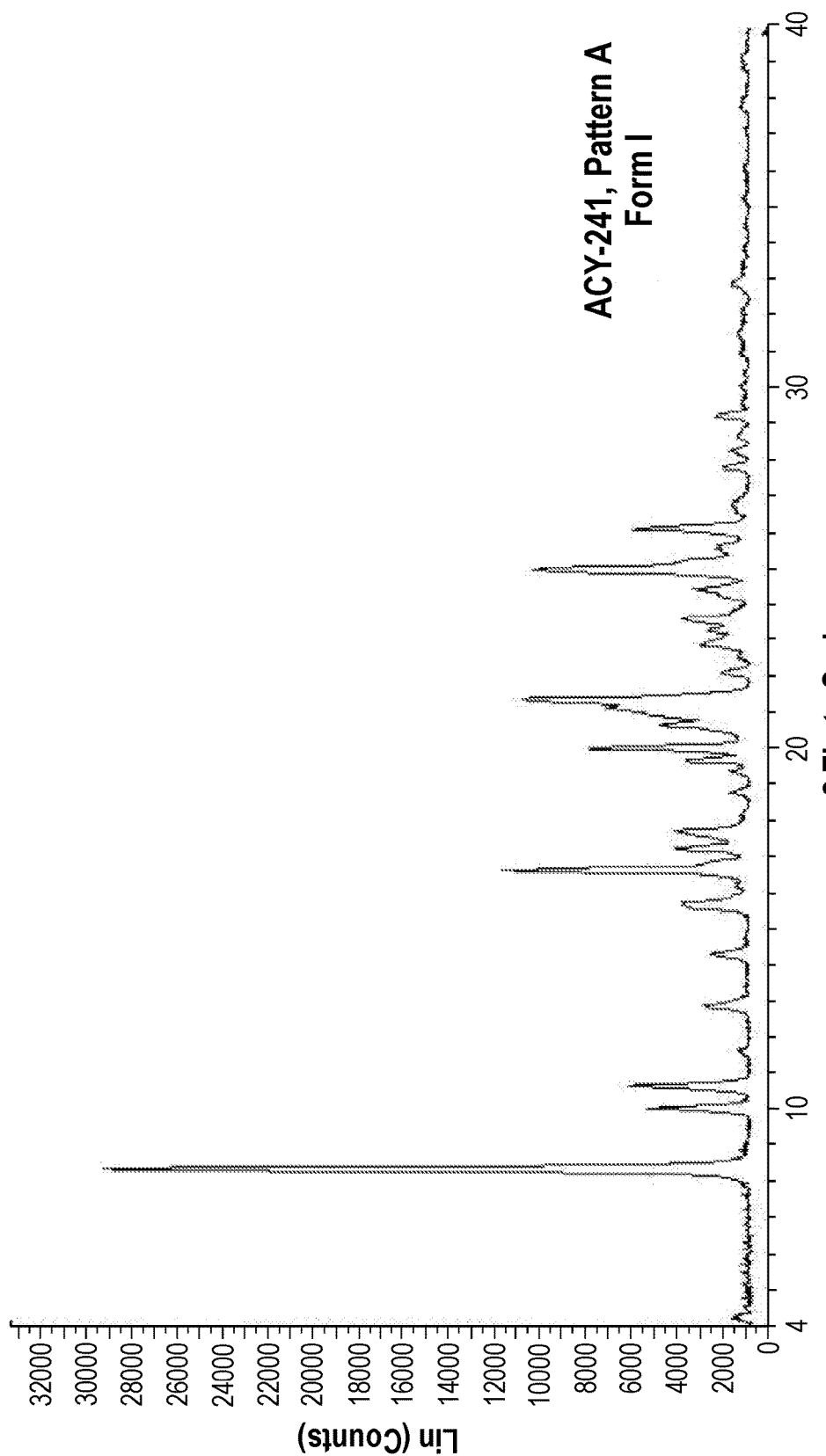
FIG. 8 depicts the XRPD pattern (Pattern A) of compound (I), Form I.

Peak list for Pattern A (FIG. 8)

| Angle (2θ) degree | Intensity % | d value (Å) |
|---|---|---|
| 8.31 | 100 | 10.626 |
| 10.00 | 15.3 | 8.834 |
| 10.62 | 17.8 | 8.327 |
| 12.82 | 6.4 | 6.898 |
| 15.62 | 9.2 | 5.667 |
| 16.60 | 36.4 | 5.337 |
| 17.20 | 9.4 | 5.152 |
| 17.67 | 9.5 | 5.014 |
| 19.63 | 8.5 | 4.518 |
| 19.99 | 22.7 | 4.438 |
| 20.64 | 10.1 | 4.300 |
| 21.08 | 18.2 | 4.210 |
| 21.33 | 32.4 | 4.162 |
| 24.41 | 7.3 | 3.643 |
| 24.95 | 30.7 | 3.566 |
| 26.08 | 16.1 | 3.413 |

Figure 9:
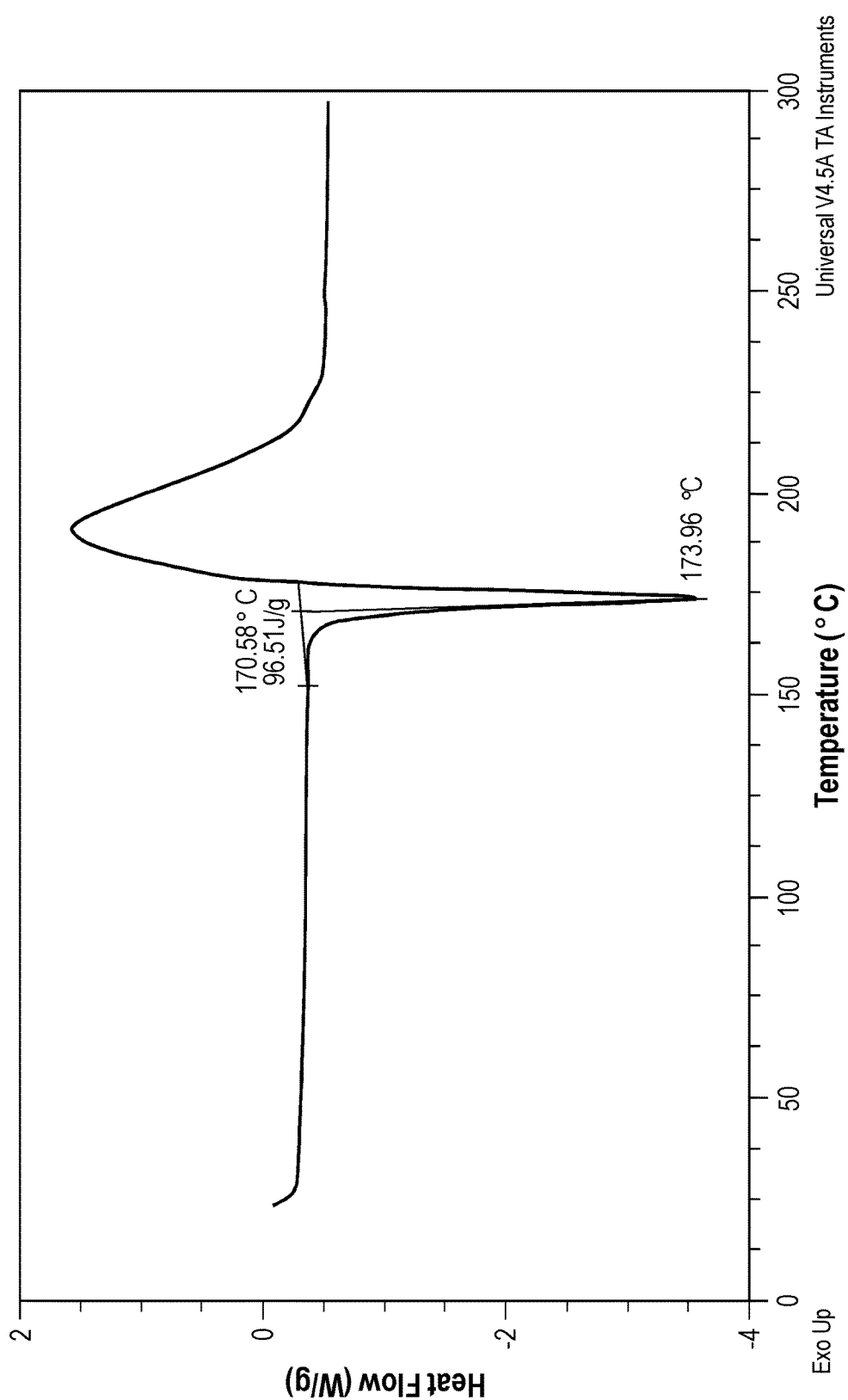
FIG. 9 depicts the DSC graph of compound (I), Form I.
Figure 10:
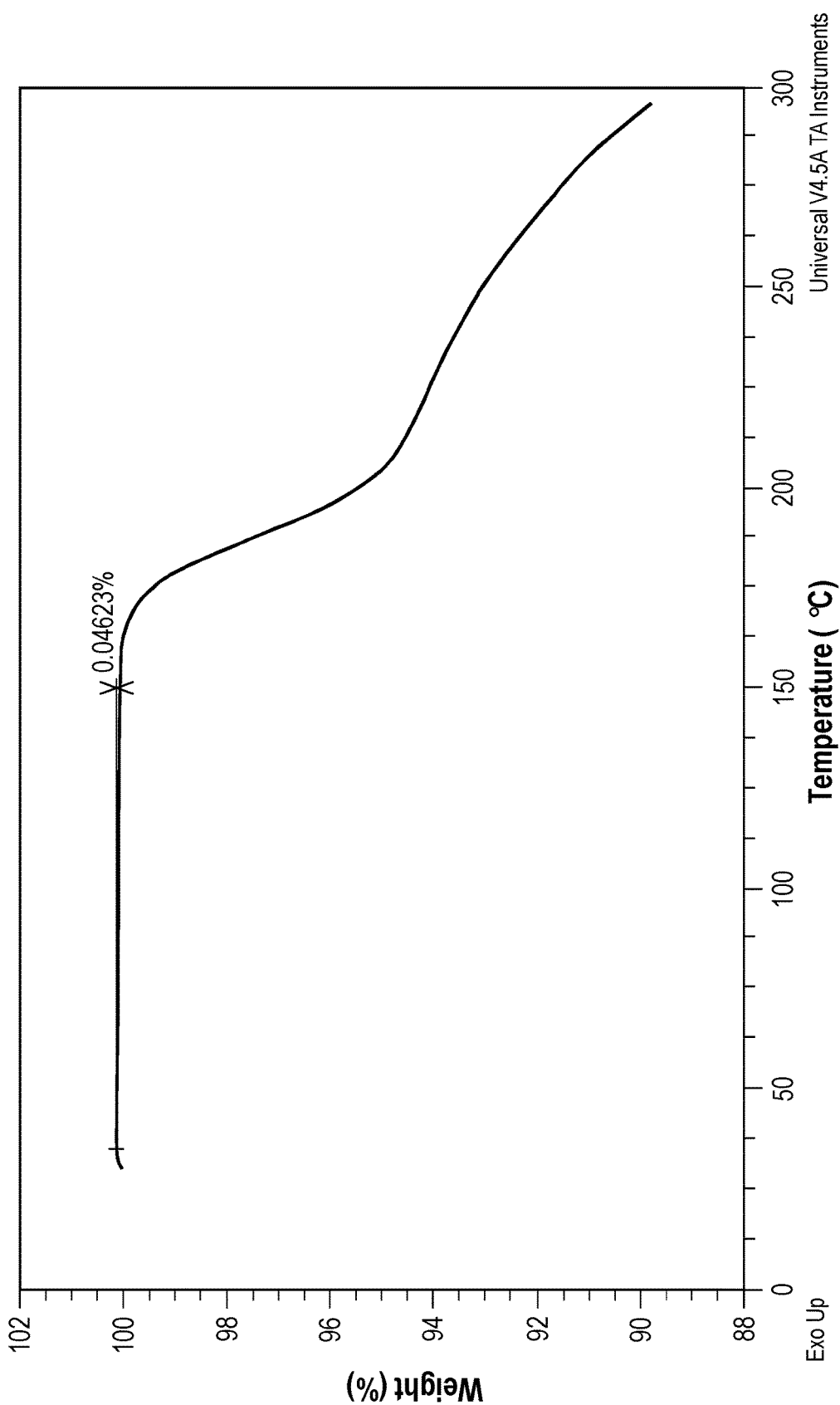
FIG. 10 depicts the TGA thermogram of compound (I), Form I.

Form I can also be characterized by differential scanning calorimetry (DSC) and thermal gravimetric analysis (TGA) (see FIGS. 8 and 9, respectively). The dynamic vapor sorption (DVS) experiment revealed less than 0.2% of moisture uptake by Compound (I), Form I/Pattern A, when subjected to relative humidity between 0-95 percent and no change in the crystalline form was observed. DSC analysis also indicated an endothermic thermal event (melting point) at around 173° C., followed by an exothermic event (possible decomposition). TGA analysis revealed that there is less than 0.1% weight loss in the sample from 35 to 150° C.

Karl Fischer (KF) titration also revealed less than <1% of water content.

Form I of compound (I) can be prepared from amorphous compound (I), or from another crystalline form of compound (I), by stirring for 8-16 hours (e.g., overnight) in a slurry of ethanol.

Figure 11:
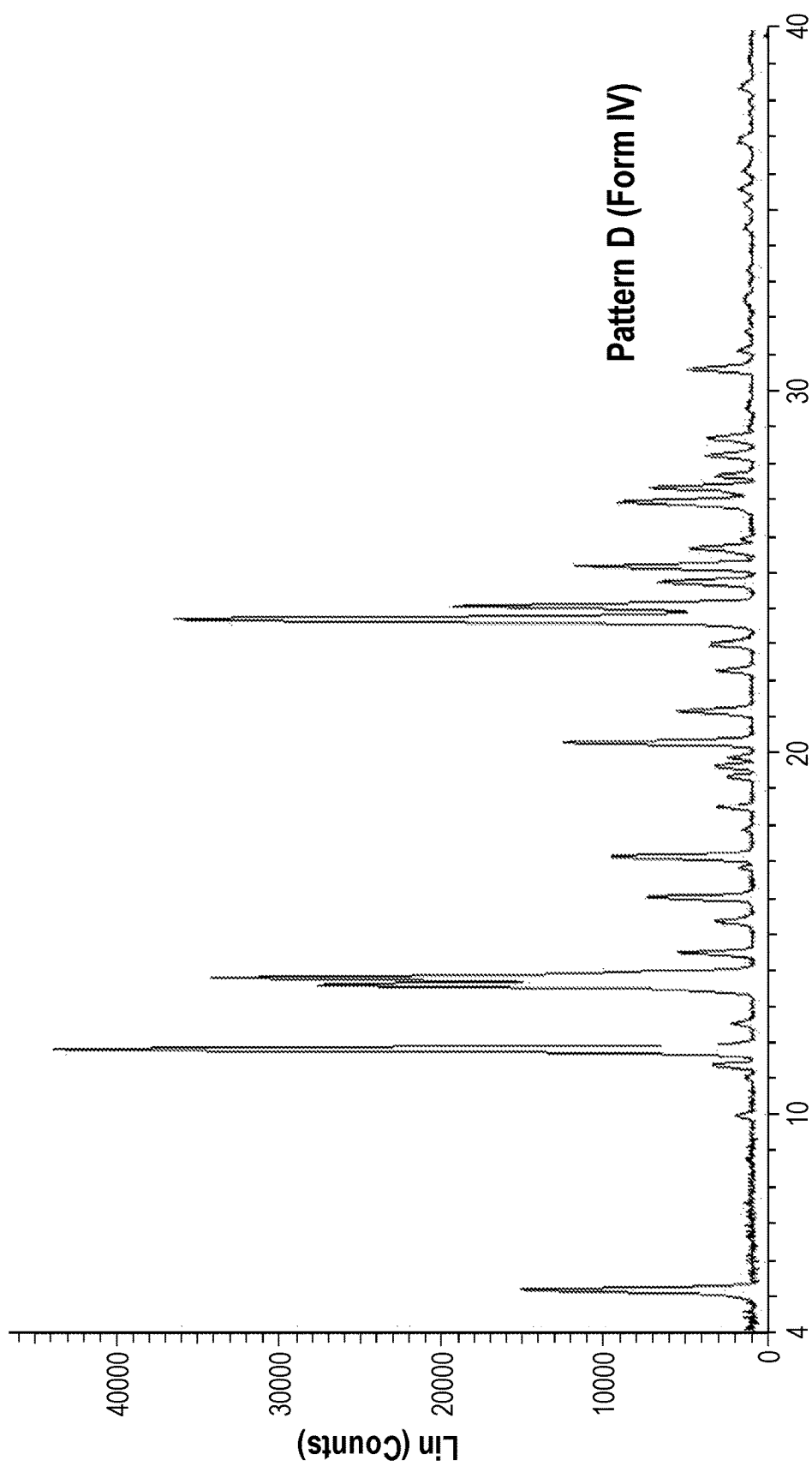
FIG. 11 depicts the XRPD pattern (Pattern D) of compound (I), Form IV.

II. Form IV/Pattern D 2-((2-chlorophenyl)(phenyl)amino)-N-(7-(hydroxyamino)-7-oxoheptyl)pyrimidine-5-carboxamide (i.e., compound (I)) may exist in crystal Form IV (referred to herein as "Form IV"). Form IV can be characterized using X-ray powder diffraction (XRPD). The XRPD pattern of Form IV is shown in FIG. 11, and is referred to as "Pattern D".

TABLE 6

Peak list for Pattern D XRPD, Form IV

| Angle (2θ) degree | Intensity % | d value (Å) |
|---|---|---|
| 5.13 | 32.9 | 17.212 |
| 11.78 | 100 | 7.508 |
| 13.60 | 61.8 | 6.506 |
| 13.80 | 77.2 | 6.412 |
| 14.48 | 10.4 | 6.112 |
| 16.01 | 15 | 5.532 |
| 17.13 | 19.9 | 5.172 |
| 20.30 | 26.7 | 4.370 |

TABLE 6-continued

Peak list for Pattern D XRPD, Form IV

| Angle (2θ) degree | Intensity % | d value (Å) |
|---|---|---|
| 21.16 | 10.6 | 4.195 |
| 23.69 | 82.4 | 3.753 |
| 24.05 | 42.7 | 3.698 |
| 24.70 | 13.3 | 3.601 |
| 25.16 | 25.1 | 3.536 |
| 26.95 | 19 | 3.306 |
| 27.36 | 14.3 | 3.258 |
| 30.61 | 9.1 | 2.918 |

The invention claimed is:

1. A method of making compound Ia comprising the following steps:

(1) reacting compound 1a:

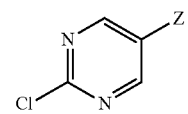

1a with an aniline and an acid to form compound 11a:

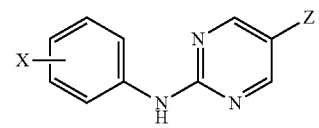

11a wherein:

X is selected from fluorine, chlorine, bromine and iodine;

Z is —CO$_2$R; and

R is C$_1$-C$_6$ alkyl;

(2) reacting compound 11a with iodobenzene in the presence of elemental copper to obtain compound 3a:

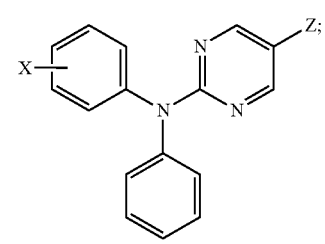

3a (3) reacting compound 3a with water to obtain compound 4a:

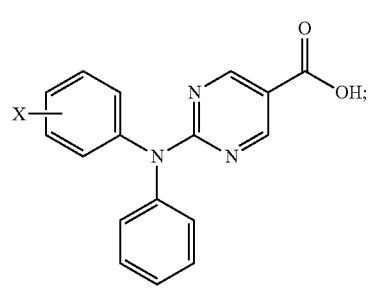
4a (4) reacting compound 4a with a $C_7$ alkyl amine in the presence of hydroxybenzotriazole to obtain compound 5a:

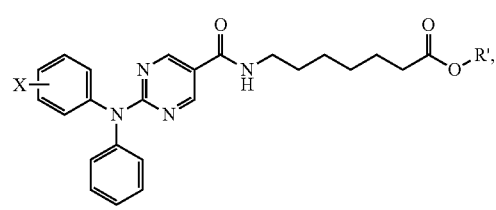
5a wherein R' is $C_1$-$C_6$ alkyl; and (5) reacting compound 5a with an alkoxide base to obtain compound (Ia), or a salt thereof:

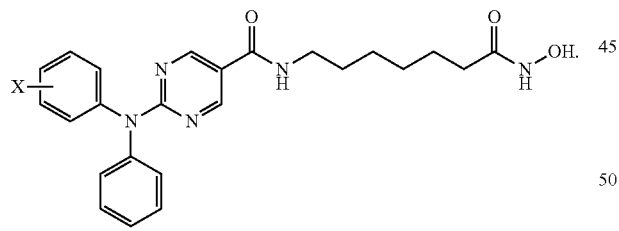
(Ia)

2. The method of claim 1, wherein R' is methyl.

3. The method of claim 1, wherein making compound 11a further comprises reacting compound 1a:

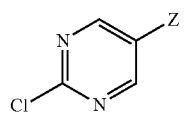
1a with an aniline and an acid, followed by deprotonation by a base to form compound 11a:

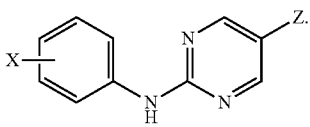
11a

4. The method of claim 1, wherein making compound 3a further comprises reacting compound 11a:

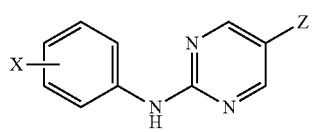
11a with iodobenzene in the presence of elemental copper and a base to obtain compound 3a:

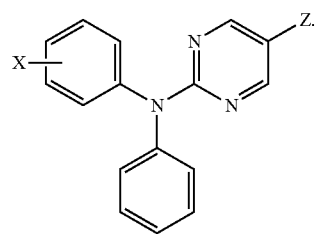
3a

5. The method of claim 1, wherein making compound 4a further comprises reacting compound 3a:

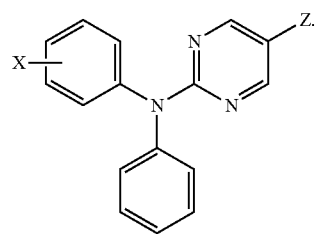
3a with water, followed by reacting with acid, to obtain compound 4a:

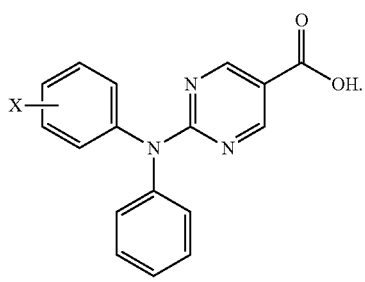
4a

6. The method of claim 1, wherein making compound 5a further comprises reacting compound 4a:

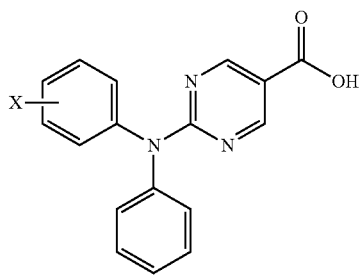

4a with a C₇ alkyl amine in the presence of hydroxybenzotriazole and 1-ethyl-3-(3-dimethylaminopropyl)carbodiimide to obtain compound 5a:

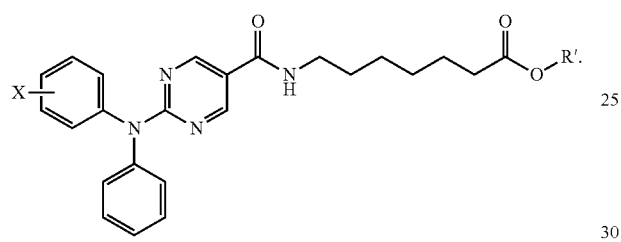

5a

7. The method of claim 1, wherein making compound Ia further comprises reacting compound 5a:

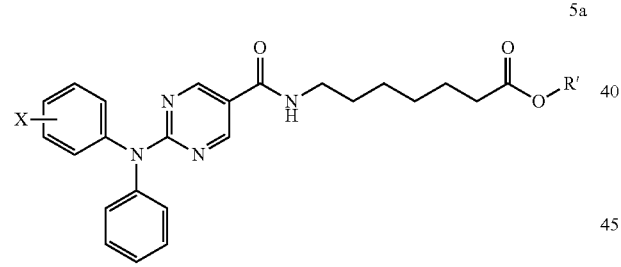

5a with an alkoxide base in the presence of hydroxylamine hydrochloride to obtain compound (Ia), or a salt thereof:

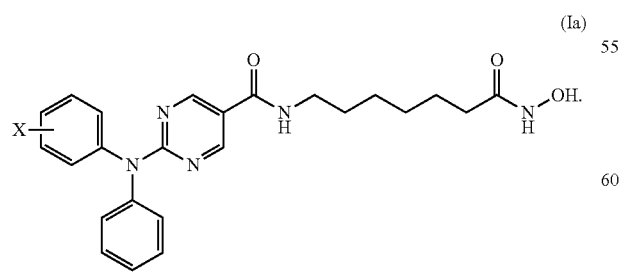

(Ia)

8. A method of making compound I comprising the following steps:

(1) reacting compound 1b:

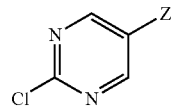

1b with 2-chloroaniline and an acid to form compound 11b:

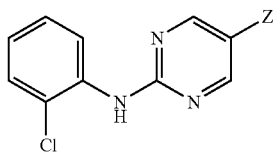

11b wherein:
Z is —CO₂R; and
R is $C_1$-$C_6$ alkyl;

(2) reacting compound 11b with iodobenzene in the presence of elemental copper to obtain compound 3b:

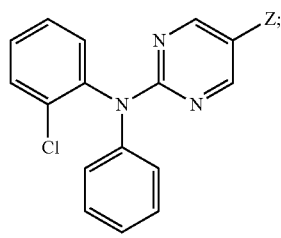

3b (3) reacting compound 3b with water to obtain compound 4:

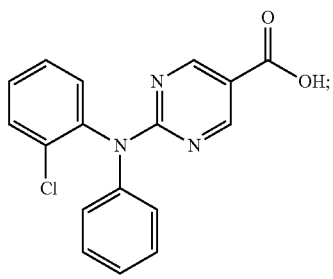

4

(4) reacting compound 4 with a C₇ alkyl amine in the presence of hydroxybenzotriazole to obtain compound 5b:

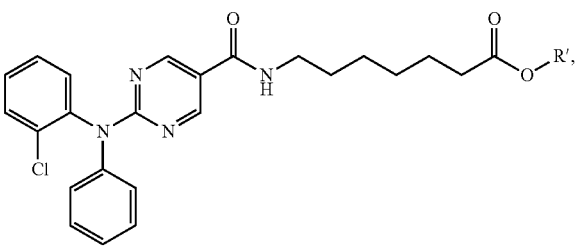

5b wherein R' is $C_1$-$C_6$ alkyl; and (5) reacting compound 5a with an alkoxide base to obtain compound (I), or a salt thereof:

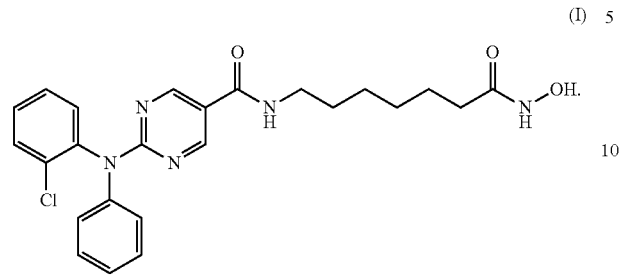

9. The method of claim 8, wherein R' is methyl.

10. The method of claim 8, wherein making compound 11b further comprises reacting compound 1b:

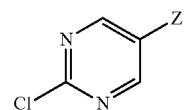

with 2-chloroaniline and an acid, followed by deprotonation by a base to form compound 11b:

11. The method of claim 8, wherein making compound 3b further comprises reacting compound 11b:

with iodobenzene in the presence of elemental copper and a base to obtain compound 3a:

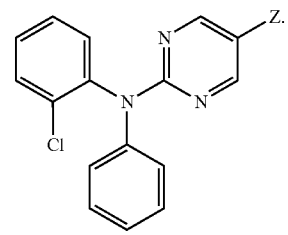

12. The method of claim 8, wherein making compound 4 further comprises reacting compound 3b:

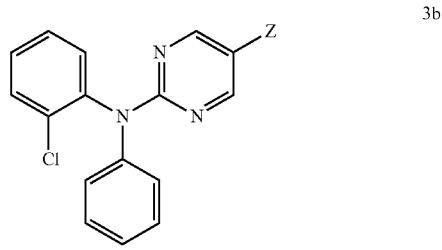

with water, followed by reacting with acid, to obtain compound 4:

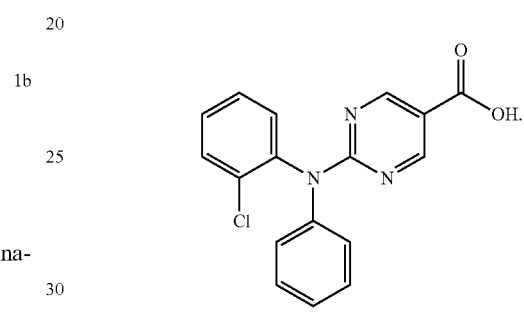

13. The method of claim 8, wherein making compound 5b further comprises reacting compound 4:

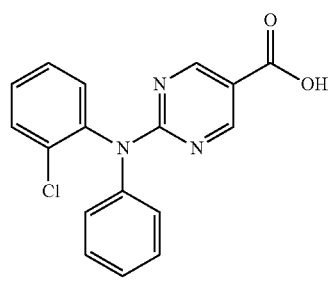

with a $C_7$ alkyl amine in the presence of hydroxybenzotriazole and 1-ethyl-3-(3-dimethylaminopropyl)carbodiimide to obtain compound 5b:

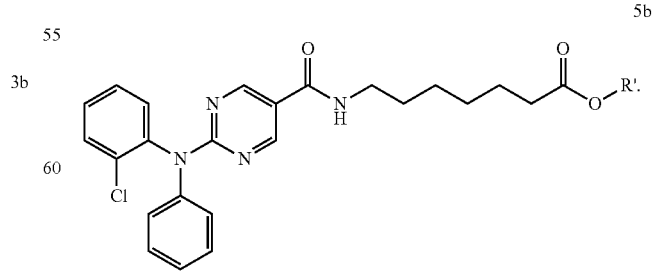

14. The method of claim 8, wherein making compound I further comprises reacting compound 5b:

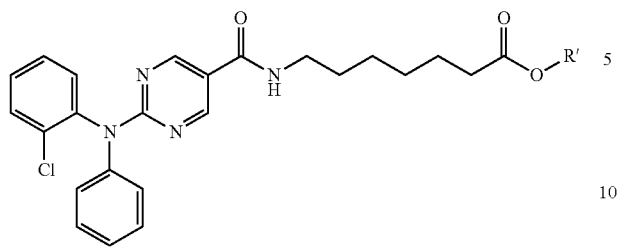

with an alkoxide base in the presence of hydroxylamine hydrochloride to obtain compound (I), or a salt thereof:

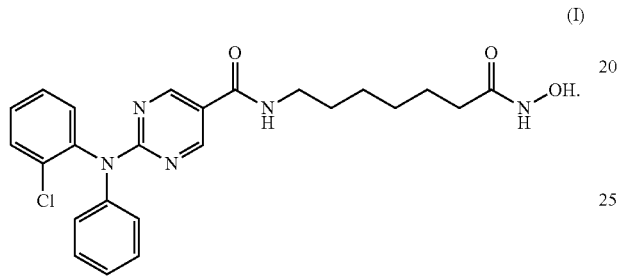

15. A method of making compound (I) comprising the following steps:

(1) reacting ethyl 2-chloropyrimidine-5-carboxylate with 2-chloroaniline in the presence of an alcohol solvent to obtain compound 11:

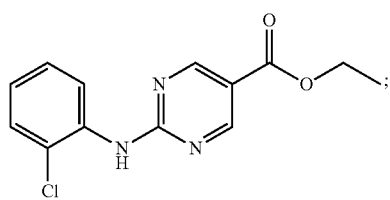

(2) reacting compound 11 with iodobenzene in the presence of elemental copper to obtain compound 3:

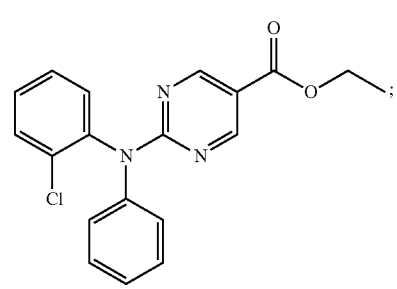

(3) reacting compound 3 with water, followed by reacting with acid, to obtain compound 4:

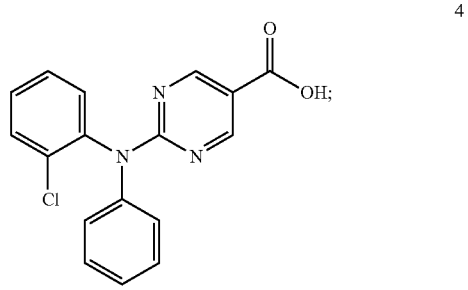 [SMILES: O=C(O)c1cnc(N(c2ccccc2)c2ccccc2Cl)nc1]

(4) reacting compound 4 with methyl 7-aminoheptanoate in the presence of hydroxybenzotriazole and 1-ethyl-3-(3-dimethylaminopropyl)carbodiimide to obtain compound 5:

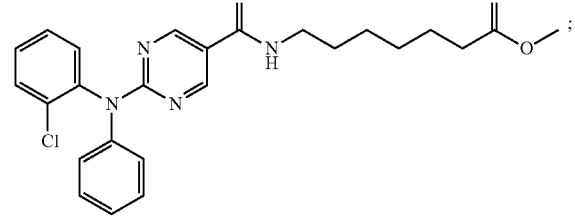

and (5) reacting compound 5 with hydroxylamine, or a salt thereof, and an alkoxide base in an alcohol solvent to obtain compound (I), or a salt thereof:

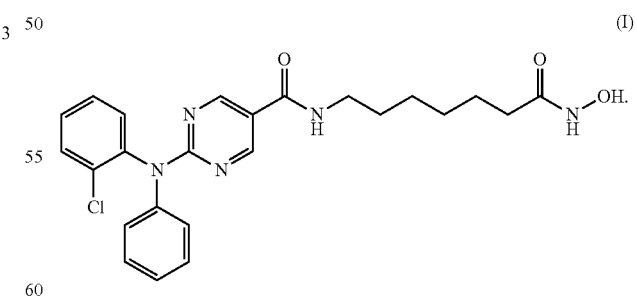

* * * * *